(12) United States Patent
MacCuish et al.

(10) Patent No.: US 6,625,585 B1
(45) Date of Patent: Sep. 23, 2003

(54) METHOD AND SYSTEM FOR ARTIFICIAL INTELLIGENCE DIRECTED LEAD DISCOVERY THOUGH MULTI-DOMAIN AGGLOMERATIVE CLUSTERING

(75) Inventors: John D. MacCuish, Santa Fe, NM (US); Christodoulos A. Nicolaou, Limassaol (CY)

(73) Assignee: Bioreason, Inc., Santa Fe, NM (US)

( * ) Notice: Subject to any disclaimer, the term of this patent is extended or adjusted under 35 U.S.C. 154(b) by 0 days.

(21) Appl. No.: 09/549,746

(22) Filed: Apr. 14, 2000

Related U.S. Application Data

(60) Provisional application No. 60/183,383, filed on Feb. 18, 2000.

(51) Int. Cl.$^7$ .............................. G06E 1/00; G06F 17/00
(52) U.S. Cl. .......................................... 706/10; 706/11
(58) Field of Search ...................... 706/10, 11

(56) References Cited

U.S. PATENT DOCUMENTS

| | | | |
|---|---|---|---|
| 5,025,388 A | 6/1991 | Cramer, III et al. | |
| 5,263,120 A | 11/1993 | Bickel | |
| 5,307,287 A | 4/1994 | Cremer, III et al. | |
| 5,590,218 A | 12/1996 | Ornstein | 382/157 |
| 5,684,711 A | 11/1997 | Agrafiotis et al. | |
| 5,751,605 A | 5/1998 | Hurst et al. | |
| 5,825,909 A | * 10/1998 | Jang | 382/132 |

FOREIGN PATENT DOCUMENTS

WO    WO 98/47087    10/1998

OTHER PUBLICATIONS

Downs, G.M. and Willett, P., Similarity Searching and Clustering of Chemical–Structure Databases Using Molecular Property Data, *J. Chem. Inf. Comput. Sci.* 34:1094–1102 (1994).

Kearsley, S.K. et al., Chemical Similarity Using Physiochemical Property Descriptors, *J. Chem. Inf. Comput. Sci*, 36:118–127 (1996).

Brown, R.D., et al., Matching Two–Dimensional Chemical Graphs Using Genetic Algorithms, *J. Chem. Inf. Comput. Sci.* 34:63–70 (1994).

Brown, R.D. and Martin, Y.C., Use of Structure–Activity Data to Compare Structure–Based Clustering Methods and Descriptors for Use in Compound Selection, *J. Chem. Inf. Comput. Sci.* 36:572–584 (1996).

Discriminant Analysis and Clustering—Panel on Discriminant Analysis, Classification and Clustering. *Statistical Science* 4: 34–69 (1989).

(List continued on next page.)

*Primary Examiner*—George B. Davis
(74) *Attorney, Agent, or Firm*—McDonnell Boehnen Hulbert & Berghoff

(57) ABSTRACT

A system for helping a chemist to identify pharmacophoric mechanisms, based on a set of input data representing many chemical compounds. Given an input data set defining for each compound a feature characteristic and an activity characteristic, a computer agglomeratively clusters representations of the molecules based on their feature characteristics. The result of this process is a multi-domain pyramid structure, made up of a number of nodes each representing one or more molecules. For each node, the computer identifies a representative feature set (such as a largest substructure common among the molecules in the node) and a representative activity level (such as an average of the activity levels of the molecules in the node). The computer then provides as output to a chemist a description of all or part of the pyramid. This process thus converts a large set of raw data into an understandable and commercially useful form, which can assist the chemist in developing beneficial new pharmaceuticals.

41 Claims, 8 Drawing Sheets

OTHER PUBLICATIONS

Barnard, J.M. and Downs, G.M., Chemical Fragment Generation and Clustering Software, Product Descriptions, Jun. 27, 1996.

Regalado, A., Preclinical Strategies—Drug Development's Preclinical Bottleneck. *Start–Up*, pp26–37 (Dec. 1997).

Longman, R., Marketplace Strategies—Screening the Screeners. *Start–Up*, pp. 14–22 (Sep. 1997).

Thayer, A.M., Combinatorial Chemistry becoming core technology at drug discovery companies. *C&EN*, pp. 57–67 (Feb. 1996).

Combinatorial Chemistry—Combinatorial chemists focus on small Molecules, molecular recognition, and automation, *C & EN*, pp. 28–54 (Feb. 1996).

Kohonen, T., Self–Organizing Maps, Springer, pp. 85–144.

Goodacre, R. et al., Quantitative Alanysis of Multivariate Data using Artificial Neural Networks: A Tutorial Review and Applications to the Deconvolution of Pyrolysis Mass Spectra, *Tutorial form <> Zentralblatr fur Bakteriologie* (1999).

Chen, X. et al., Recursive Partitioning Analysis of a Large Structure–Activity Data Set Using Three–Dimensional Descriptors. *J. Chem Inf. Comput. Sci.* (1998).

James, C.A. et al., Daylight Theory Manual Daylight 4.61, Daylight Chemical Information Systems, Inc., Version 11 (Feb. 1997).

Labute, P., Binary QSAR: A new Technology for HTS and UHTS Data Analysis, Chemical Computing Group, Inc. In *Journal of the Chemical Computing Group* (1998).

From the World Wide Web: www.netsci.org, Network Science—Welcome to NetSci's Lists of Computational Chemistry Software (1999), printed Feb. 8, 1999.

From the World Wide Web: www.netsci.org, Network Science—Welcome to NetSci's Combinatorial Chemistry and Mass Screening YellowPages (1999), printed Feb. 8, 1999.

Weininger, D., SMILES, a Chemical Language and Information System, 1. Introduction to Methodology and Encoding Rules. *J. Chem. Inf. Comput. Sci.,* 28: 31–36 (1988).

Cook, D.J. et al., Knowledge Discovery from Structural Data. *Journal of Intelligence and Information Sciences*, vol. 5, No., 3, pp. 229–245 (1995).

Djoko, S. et al., An Empirical Study of Domain Knowledge and its Benefits to Substructure Discovery. In *IEEE Transactions on Knowledge and Data Engineering*, vol. 9, No. 4, pp. 1–13 (1997).

Galal, G. et al., Improving Scalability in a Knowledge Discovery System by Exploiting Parallelism. In the Proceedings of the Third International Conference on Knowledge Discovery and Data Mining, pp. 171–174 (1997).

Holder, L. B. and D. J. Cook. Discovery of Inexact Concepts from Structural Data. In *IEEE Transactions on Knowledge and Data Engineering*, vol. 5,No. 6, pp. 992–994 (1993).

Holder , L. B. et al., Fuzzy Substructure Discovery. In *Proceedings of the Ninth International Conference on Machine Learning*, pp. 218–223 (1992).

Djoko, S. et al., Analyzing the Benefits of Domain Knowledge in Substructure Discovery. In *Proceedings of the First International Conference on Knowledge Discovery and Data Mining*, pp. 75–80 (1995).

Cook, D. J. et al., Scalable Discovery of Informative Structural Concepts Using Domain Knowledge. In *IEEE Expert*, vol. 11, No. 5, pp. 59–68 (1996).

Aude, J.C. et al., Applications of the pyramidal clustering method to biological objects. Computers & Chemistry 23:301–315 (1999).

Bertrand, P., Structural Properties of Pyramidal Clustering. DIMACS Series in Discrete Mathematics and Theoretical Computer Science, 19: 35–53 (1995).

Fausett, L., Fundamentals of Neural Networks: Architectures, Algorithms, and Applications. pp. 169–188 (1994).

Godden, Jeffrey W., et al. Combinatorial Preferences Affect Molecular Similarity/Diversity Calculations Using Binary Fingerprints and Tanimoto Coefficients. *J. Chem. Inf. Comput. Sci.* 2000, vol. 40, pp. 163–166.

"Pyramids" Homepage: Including http://bioweb.pasteur.fr/docs–gensoft/pyramids/QuickStart.

From the World Wide Web: http://www.tripos.com/software/charisma.html, printed Feb. 15, 2000.

From the World Wide Wide: http://www.tripos.com/about/press/1999/1999.03.23.html, printed Feb. 15, 2000.

From the World Wide Web: http://www.daylight.com/meetings/mug2000/JmacCuish/index.html, printed Apr. 5, 2000.

From the World Wide Web: http://www.daylight.com/meetings/mug2000/JmacCuish/MugTies.html, printed Mar. 2, 2000.

van Osdol, W. W. et al., "Use of the Kohonen Self–organizing Map to Study the Mechanisms of Action of Chemotherapeutic Agents", *Journal of the National Cancer Institute*, 86:1853–1859 (1994).

Ornstein, L., "Computer Learning and the Scientific Method: A Proposed Solution to the Information Theoretical Problem of Meaning", *Journal of the Mount Sinai Hospital*, XXXII:437–494 (1965).

Barnard, J. M. and Downs, G. M., "Clustering of Chemical Structures on the Basis of Two–Dimensional Similarity Measures", *Journal of Chemical Information and Computer Sciences*, 32:644–649 (1992).

Grethe, G. and Hounshell, W. D., "Similarity Searching in the Development of New Bioactive Compounds. An Application.", *Chemical Structure Proceedings International Conference*, pp. 399–407 (1993).

King, R. D. et al., "Comparison of Artificial Intelligence Methods for Modeling Pharmaceutical Qsars", *Applied Artificial Intelligence*, 9:213–233 (1995).

Jain, K. J. et al., "Algorithms for Clustering Data", *Algorithms for Clustering Data*, pp. 96–101 (1988).

\* cited by examiner

Figure 3a

| Exemplary Starting Keys | | | |
|---|---|---|---|
| SMARTS Query | Minimum hits | Weight | Comment and corresponding MACCS definition, if any |
| [R2;r5]~[R2;r5] | 1 | 7 | 1 Any double ring, structure with the smallest ring a 5 member ring |
| [R2;r6]~[R2;r6] | 1 | 7 | 2 Any double ring structure with the smallest ring a 6 member ring |
| [!#6;r4][r4][r4][r4] | 1 | 100 | 3 QAAA@1 |
| [#4,#12,#20,#38,#56,#88] | 1 | 100 | 4 Group IIA |
| [r4] | 1 | 100 | 5 4 M ring |
| [#29,#30,#47,#48,#79,#80] | 1 | 95 | 6 group IB,IIB |
| [#8]~[#7](~[#6])~[#6] | 1 | 100 | 7 ON(C)C |
| [#16]-[#16] | 1 | 100 | 8 S-S |
| [#8]~[#6](~[#8])~[#8] | 1 | 100 | 9 OC(O)O |
| [!#6]1~*~*1 | 1 | 100 | 10 QAA@1 |
| C#C | 1 | 85 | 11 CTC |
| [#5,#13,#31,#49,#81] | 1 | 76 | 12 Group IIIA |
| [r7] | 1 | 90 | 13 7 M ring |
| [#14] | 1 | 40 | 14 Si |
| [#6]=[#6](~[!#6])~[!#6] | 1 | 56 | 15 C=C(Q)Q |
| [r3] | 1 | 80 | 16 3 M ring |
| [#7]~[#6](~[#8])~[#8] | 1 | 18 | 17 NC(O)O |
| [#7]-[#8] | 1 | 9 | 18 N-O |
| [#7]~[#6](~[#7])~[#7] | 1 | 45 | 19 NC(N)N |
| [#6;R]=[#6;R](@*)@* | 1 | 35 | 20 C$=C($A)($A) |
| [#53] | 1 | 40 | 21 I |
| [!#6][CH2][!#6] | 1 | 57 | 22 QCH2Q |
| [#15] | 1 | 20 | 23 P |
| [#6]~[!#6](~[#6])(~[#6])~* | 1 | 29 | 24 CQ(C)(C)A |
| [!#6]~[#9,#17,#35,#53] | 1 | 23 | 25 QX |
| [#6]~[#16]~[#7] | 1 | 50 | 26 CSN |
| [#7]~[#16] | 1 | 46 | 27 NS |
| [CH2]=,:* | 1 | 26 | 28 CH2=A |
| [#16;r] | 1 | 30 | 29 S heterocycle |
| [#7]~[#6](~[#8])~[#7] | 1 | 12 | 30 NC(O)N |
| [#7]~[#6](~[#6])~[#7] | 1 | 20 | 31 NC(C)N |
| [#8]~[#16](~[#8])~[#8] | 1 | 25 | 32 OS(O)O |
| [#16]-[#8] | 1 | 25 | 33 S-O |
| C#N | 1 | 24 | 34 CTN |
| [#9] | 1 | 12 | 35 F |
| [!#6;H1,H2,H3]~*~[!#6;H1,H2,H3] | 1 | 10 | 36 QHAQH |
| [#6]=[#6]~[#7] | 1 | 14 | 37 C=CN |
| [#35] | 1 | 14 | 38 Br |
| [#16]~*~[#7] | 1 | 15 | 39 SAN |

Figure 3b

| Exemplary Starting Keys Cont. | | | |
|---|---|---|---|
| SMARTS Query | Minimum hits | Weight | Comment and corresponding MACCS definition, if any |
| [#8]~[!#6](~[#8])~[#8] | 1 | 10 | 40 OQ(O)O |
| [-,--,---,+,++,+++] | 1 | 6 | 41 charge |
| [#6]=[#6](~[#6])~[#6] | 1 | 11 | 42 C=C(C)C |
| [#6]~[#16]~[#8] | 1 | 14 | 43 CSO |
| [#7]~[#7] | 1 | 12 | 44 NN |
| [!#6;H1,H2,H3]~*~*~*[!#6;H1,H2,H3] | 1 | 10 | 45 QHAAAQH |
| [!#6;H1,H2,H3]~*~*[!#6;H1,H2,H3] | 1 | 8 | 46 QHAAQH |
| [#8]~[#16]~[#8] | 1 | 13 | 47 OSO |
| [#8]~[#7](~[#8])~[#6] | 1 | 11 | 48 ON(O)C |
| [#8;r] | 1 | 8 | 49 O heterocycle |
| [!#6]~[#16]~[!#6] | 1 | 12 | 50 QSQ |
| [#16]!:*:* | 1 | 12 | 51 Snot%A%A |
| [#16]=,:[#8] | 1 | 13 | 52 S=O |
| *~[#16](~*)~* | 1 | 12 | 53 AS(A)A |
| *@*!@*@* | 1 | 11 | 54 A$A!A$A |
| [#7]=,:[#8] | 1 | 11 | 55 N=O |
| *@*!@[#16] | 1 | 11 | 56 A$A!S |
| [#6]:[#7] | 1 | 12 | 57 C%N |
| [#6][#6]([#6])([#6])* | 1 | 9 | 58 CC(C)(C)A |
| [!#6]~[#16] | 1 | 11 | 59 QS |
| [!#6;H1,H2,H3]~[!#6;H1,H2,H3] | 1 | 8 | 60 QHQH(&..) |
| [!#6]~[!#6;H1,H2,H3] | 1 | 8 | 61 QQH |
| [!#6]~[#7]~[!#6] | 1 | 9 | 62 QNQ |
| [#7]~[#8] | 1 | 9 | 63 NO |
| [#8]~*~*~[#8] | 1 | 7 | 64 OAAO |
| [#16]=,:* | 1 | 8 | 65 S=A |
| [#6H3]~*~[#6H3] | 1 | 6 | 66 CH3ACH3 |
| *!@[#7]@* | 1 | 8 | 67 A!N$A |
| [#6]=[#6](~*)~* | 1 | 6 | 68 C=C(A)A |
| [#7]~*~[#7] | 1 | 5 | 69 NAN |
| [#6]=[#7] | 1 | 6 | 70 C=N |
| [#7]~*~*~[#7] | 1 | 6 | 71 NAAN |
| [#7]~*~*~*~[#7] | 1 | 6 | 72 NAAAN |
| [#16]~*(~*)~* | 1 | 7 | 73 SA(A)A |
| *~[#6H2]~[!#6;H1,H2,H3,H4] | 1 | 6 | 74 ACH2QH |
| [!#6;!#1;r5]1~[r5]~[r5]~[r5]~[r5]1 | 1 | 5 | 75 QAAAA@1 |
| [#7;H2,H3,H4] | 1 | 6 | 76 NH2 |
| [#6]~[#7](~[#6])~[#6] | 1 | 5 | 77 CN(C)C |
| [#6;H2,H3]~[!#6]~[#6;H2,H3] | 1 | 5 | 78 CH2QCH2 |
| [#9,#17,#35,#53]!@*@* | 1 | 4 | 79 X!A$A |

Figure 3c

| Exemplary Starting Keys Cont. | | | |
|---|---|---|---|
| SMARTS Query | Minimum hits | Weight | Comment and corresponding MACCS definition, if any |
| [#16] | 1 | 5 | 80 S |
| [#8]~*~*~*~[#8] | 1 | 4 | 81 OAAAO |
| [!#6;H1,H2,H3]~*~*~[#6;H2]~* | 1 | 4 | 82 QHAACH2A |
| [!#6;H1,H2,H3]~*~*~*[#6;H2]* | 1 | 4 | 83 QHAAACH2A |
| [#8]~[#6](~[#7])~[#6] | 1 | 4 | 84 OC(N)C |
| [!#6;!#1]~(CH3) | 1 | 4 | 85 QCH3 |
| [!#6;!#1]~[#7] | 1 | 4 | 86 QN |
| [#7]~*~*~[#8] | 1 | 4 | 87 NAAO |
| [r5] | 1 | 4 | 88 5M ring |
| [#7]~*~*~*~[#8] | 1 | 5 | 89 NAAAO |
| [!#6]1~*~*~*~*~*1 | 1 | 5 | 90 QAAAAA@1 |
| [#6]=[#6] | 1 | 4 | 91 C=C (does not hit aromatic) |
| *~[#6H2]~[#7] | 1 | 4 | 92 ACH2N |
| [r8,r9,r10,r11,r12,r13,r14] | 1 | 4 | 93 8M ring or larger |
| [!#6]~[#8] | 1 | 3 | 94 QO |
| [#17] | 1 | 4 | 95 CL |
| [!#6;H1,H2,H3]~*~[CH2]~* | 1 | 4 | 96 QHACH2A |
| *@*(@*)@* | 1 | 4 | 97 A$A($A)$A |
| [!#6;!#1]~*(~[!#6;!#1])~[!#6;!#1] | 1 | 2 | 98 QA(Q)Q |
| [#9,#17,#35,#53]~*(~*)~* | 1 | 3 | 99 XA(A)A |
| [CH3]~*~*~*~[CH2]~[!#1] | 1 | 4 | 100 CH3AAACH2A |
| *~[#6;H3,H2]~[#8] | 1 | 4 | 101 ACH2O |
| [#7]~[#6]~[#8] | 1 | 3 | 102 NCO |
| [#7]~*~[#6;H2]~* | 1 | 4 | 103 NACH2A |
| *~*(~*)(~*)~* | 1 | 3 | 104 AA(A)(A)A |
| [#8]!:*:* | 1 | 4 | 105 Onot%A%A |
| [CH3]~[#6;H2]~* | 1 | 3 | 106 CH3CH2A |
| [CH3]~*~[#6;H2]~* | 1 | 3 | 107 CH3ACH2A |
| [CH3]~*~*~[#6;H2]~* | 1 | 3 | 108 CH3AACH2A |
| [#7]~*~[#8] | 1 | 2 | 109 NAO |
| *~[CH2][CH2]~* | 3 | 3 | 110 ACH2CH2A > 1 |
| [#7]=,:* | 1 | 3 | 111 N=A |
| [!#6&r] | 2 | 3 | 112 heterocycle atom > 1 & other features |
| [#7&r] | 1 | 4 | 113 N heterocycle |
| *~[#7](~*)~* | 1 | 3 | 114 AN(A)A |
| [#8]~[#6]~[#8] | 1 | 3 | 115 OCO |
| [!#6]~[!#6] | 1 | 2 | 116 QQ |
| a | 7 | 2 | 117 aromatic ring > 1 |
| *!@[#8]!@* | 1 | 2 | 118 A!O!A |

Figure 3d

| Exemplary Starting Keys Cont. | | | |
|---|---|---|---|
| SMARTS Query | Minimum hits | Weight | Comment and corresponding MACCS definition, if any |
| *@*!@[#8] | 2 | 2 | 119 A$A!O > 1 & ... |
| *[CH2]*~*~*[CH2]* | 1 | 3 | 120 ACH2AAACH2A |
| *~[#6&H2]~*~*~[#6&H2]~* | 1 | 3 | 121 ACH2AACH2A |
| [!#6]~[!#6] | 2 | 2 | 122 QQ > 1 |
| [!#6;H1,H2,H3,H4] | 2 | 2 | 123 QH > 1 |
| [#8]~*[CH2]* | 1 | 2 | 124 OACH2A |
| *@*!@[#7] | 1 | 2 | 125 A$A!N |
| [#9,#17,#35,#53] | 1 | 2 | 126 X (halogen) |
| [#7]!:*:* | 1 | 2 | 127 Nnot%A%A |
| [#8]=,:* | 2 | 2 | 128 O=A>1 |
| [!#6&r] | 1 | 3 | 129 heterocycle |
| [!#6]~[CH2]~* | 2 | 2 | 130 QCH2A>1 & ... |
| [#8;H1,H2] | 1 | 2 | 131 OH |
| [#8] | 4 | 2 | 132 O > 3 and other features .. |
| [CH3] | 3 | 2 | 133 CH3 > 2 |
| [#7] | 2 | 2 | 134 N>1 |
| *@*!@[#8] | 1 | 2 | 135 A$A!O |
| *!:*:*!:* | 1 | 2 | 136 Anot%A%Anot%A |
| [r6] | 7 | 2 | 137 6 M ring > 1 |
| [#8] | 3 | 2 | 138 O > 2 |
| *~[CH2]~[CH2]~* | 1 | 2 | 139 ACH2CH2A |
| *~[!#6](~*)~* | 1 | 2 | 140 AQ(A)A |
| [CH3] | 2 | 2 | 141 CH3 > 1 |
| *!@*@*!@* | 1 | 2 | 142 A!A$A!A |
| [#7;H1,H2,H3,H4] | 1 | 2 | 143 NH |
| [#8]~[#6](~[#6])~[#6] | 1 | 2 | 144 OC(C)C |
| [!#6][CH2]* | 1 | 2 | 145 QCH2A |
| [#6]=,:O | 1 | 1 | 146 C=O |
| *!@[CH2]!@* | 1 | 1 | 147 A!CH2!A |
| [#7]~*(~*)~* | 1 | 1 | 148 NA(A)A |
| [#6]-[#8] | 1 | 1 | 149 C-O |
| [#6]-,:[#7] | 1 | 1 | 150 C-N |
| [#8] | 2 | 1 | 151 O > 1 |
| [CH3] | 1 | 1 | 152 CH3 |
| [#7] | 1 | 1 | 153 N |
| a | 1 | 1 | 154 aromatic |
| [r6] | 1 | 1 | 155 6 member ring |
| [#8] | 1 | 1 | 156 O |
| R | 1 | 1 | 157 ring |

METHOD AND SYSTEM FOR ARTIFICIAL INTELLIGENCE DIRECTED LEAD DISCOVERY THOUGH MULTI-DOMAIN AGGLOMERATIVE CLUSTERING

RELATED APPLICATIONS

The application claims priority to U.S. Provisional Patent Application No. 60/183,383, entitled "Method and System for Artificial Intelligence Directed Lead Discovery Through Multi-Domain Agglomerative Clustering," filed by John D. MacCuish and Christodoulos A. Nicolaou on Feb. 18, 2000, which is assigned to the owner of the present invention, and the entirety of which is hereby incorporated by reference.

This application also claims priority to U.S. patent application Ser. No. 09/506,975, entitled "Method and System for Artificial Intelligence Lead Discovery Through Multi-Domain Clustering," filed by Christodoulos A. Nicolaou, Brian P. Kelley, Ruth F. Nutt, and Susan I. Bassett on Feb. 18, 2000, which is also assigned to the owner of the present invention, and the entirety of which is also hereby incorporated by reference.

In addition, this application relates to the subject matter of U.S. Provisional Patent Application No. 60/120,701, entitled "Artificial Intelligence Directed Lead Discovery," filed by Susan I. Bassett, Andrew P. Dalke, John W. Elling, Brian P. Kelley, Christodoulos A. Nicolaou, and Ruth F. Nutt on Feb. 19, 1999, the entirety of which is also hereby incorporated by reference.

COPYRIGHT

A portion of the disclosure of this patent document contains material that is subject to copyright protection. The copyright owner has no objection to the facsimile reproduction by anyone of the patent disclosure, as it appears in the Patent and Trademark Office patent files or records, but otherwise reserves all copyright rights whatsoever.

BACKGROUND OF THE INVENTION

1. Field of the Invention

The present invention relates to computer-based analysis of data and to computer-based correlation of data features with data responses, in order to determine or predict which features correlate with or are likely to result in one or more responses. The invention is particularly suitable for use in the fields of chemistry, biology and genetics, such as to facilitate computer-based correlation of chemical structures with observed or predicted pharmacophoric activity. More particularly, the invention is useful in facilitating identification and development of potentially beneficial new drugs.

2. Description of Related Art

The global biotech and pharmaceutical industry is a $200 billion/year business. Most of the estimated $13 billion R&D spending in this industry is focused on discovering and developing prescription drugs. Current R&D effort is characterized by low drug discovery rates and long time-to-market.

In an effort to accelerate drug discovery, biotech and pharmaceutical firms are turning to robotics and automation. The old methods of rationally designing molecules using known structural relationships are being supplanted by a shotgun approach of rapidly screening it hundreds of thousands of molecules for biological activity. High Throughput Screening (HTS) is being used to test large numbers of molecules for biological activity. The primary goal is to identify hits or leads, which are molecules that affect a particular biological target in the desired manner. For instance and without limitation, a lead may be a chemical structure that binds particularly well to a protein.

Automated HTS systems are large, highly automated liquid handling and detection systems that allow thousands of molecules to be screened for biological activity against a test assay. Several pharmaceutical and biotech companies have developed systems that can perform hundreds of thousands of screens per day.

The increasing use of HTS is being driven by a number of other developments in the industry. The greater the number and diversity of molecules that are run through screens, the more successful HTS is likely to be. This fact has propelled rapid developments in molecule library collection and creation. Combinatorial chemistry systems have been developed that can automatically create hundreds of thousands of new molecules. Combinatorial chemistry is performed in large automated systems that are capable of synthesizing a wide variety of small organic molecules using combinations of "building block" reagents. HTS systems are the only way that the enormous volume of new molecules generated by combinatorial chemistry systems can be tested for biological activity. Another force driving the increased use of HTS is the Human Genome program and the companion field of bioinformatics that is enabling the rapid identification of gene function and accelerating the discovery of therapeutic targets. Companies do not have the resources to develop an exhaustive understanding of each potential therapeutic target. Rather, pharmaceutical and biotech companies use HTS to quickly find molecules that affect the target and may lead to the discovery of a new drug.

High throughput screening does not directly identify a drug. Rather the primary role of HTS is to detect lead molecules and supply directions for their optimization. This limitation exists because many properties critical to the development of a successful drug cannot be assessed by HTS. For example, HTS cannot evaluate the bioavailability, pharmacokinetics, toxicity, or specificity of an active molecule. Thus, further studies of the molecules identified by HTS are required in order to identify a potential lead to a new drug.

The further study, a process called lead discovery, is a time- and resource-intensive task. High throughput screening of a large library of molecules typically identifies thousands of molecules with biological activity that must be evaluated by a pharmaceutical chemist. Those molecules that are selected as candidates for use as a drug are studied to build an understanding of the mechanism by which they interact with the assay. Scientists try to determine which molecular properties correlate with high activity of the molecules in the screening assay. Using the drug leads and this mechanism information, chemists then try to identify, synthesize and test molecules analogous to the leads that have enhanced drug-like effect and/or reduced undesirable characteristics in a process called lead optimization. Ideally, the end result of the screening, lead discovery, and lead optimization is the development of a new drug for clinical testing.

As the number of molecules in the test library and the number of therapeutic target assays exponentially increase, lead discovery and lead optimization have become the new bottleneck in drug discovery using HTS systems. Because of the large number of HTS results that must be analyzed, scientists often seek only first-order results such as the identification of molecules in the library that exhibit high assay activity. In one such method, for instance, all of the molecules in the data set are divided into groups based on common properties of their molecular structures. An analysis is then made to determine which groups contain molecules with high activity levels and which groups contain molecules with low activity levels. Those groups representing high activity levels are then deemed to be useful groups. Commonly, the analysis will stop at this point, leaving chemists to analyze the members of the active groups in search of new or optimized leads.

In another method, a more extensive automated analysis is conducted in an effort to partition the molecules into groups of particular interest and particularly to derive structure-activity relationship rules. For instance, well known recursive partitioning techniques, commonly referred to as classification trees, may be used to iteratively partition a data set (such as results of HTS or other automated chemical synthesis) into active classes. The data set includes molecules and indicia of empirically determined potency (activity-level) per molecule.

According to this method, a set of descriptors is first generated, each indicating a structural feature that can be described as present or absent in a given molecule. For each molecule, a bit string is then built, indicating whether the molecule has each particular descriptor (1-bit) or not (0-bit). These strings are then configured as a matrix, in which each row represents a molecule and each column represents a descriptor. Recursive partitioning is then used to divide the molecules (rows) into exactly two groups according to whether the molecules have a particular "best" descriptor in common. The "best" descriptor is the descriptor that would result in the largest possible difference in average potency between those molecules containing the descriptor and those molecules not containing the descriptor.

The recursive partitioning method then continues iteratively with respect to each subdivided group, dividing each group into two groups based on a next "best" descriptor. The result of this process is a tree structure, in which some terminal nodes may contain a preponderance of inactive molecules (or molecules having relatively low potency) and other terminal nodes may contain a preponderance of active molecules (or molecules having relatively high potency) (the latter being "good terminal nodes"). Tracing the lineage of the structures defined by a good terminal node may then reveal molecular components that cooperatively reflect a high likelihood of potency.

Unfortunately, the use of recursive partitioning to partition molecules on the basis of their structural and activity similarity is limiting. For example, with the recursive partitioning analysis, each molecule can fall within only a single terminal node of the tree structure, based on one or more determinations along the way as to whether the molecule includes various descriptors known to confer activity. Consequently, if there may be more than one set of descriptors in a molecule (or set of molecules) that results in observed activity, the method may be unable to identify all of the pertinent descriptor sets.

In view of the foregoing, the inventors have discovered that a need exists for an improved method to screen HTS data.

SUMMARY OF THE INVENTION

The present invention is directed to a computer-based system (e.g., method, apparatus and/or machine) for identifying and correlating relationships between features and responses in a data set. In the chemistry field, for instance, the invention provides a computer-based system for generating (learning) structure-to-activity relationship (SAR) information and pharmacophore models for each pharmacophoric mechanism identified in the HTS screen of a diverse (heterogeneous) library. In this context, the term "mechanism" may refer to the different ways for the molecules in the library to interact with a specified target. A mechanism model or pharmacophore can be a multi-dimensional arrangement of physical and structural features that enable a molecule to interact with a target through a specific interaction with the target's active site.

As noted above, existing analysis systems typically involve (i) dividing a set of molecules into subclasses based on structural similarity and then identifying which subclass represents higher potency and is therefore of interest for further study, or (ii) dividing a set of molecules into subclasses based on differences in potency for given structural features. The existing art thus addresses the question of how well a given subclassification distinguishes active molecules from inactive molecules.

In an exemplary embodiment, a computer learns pharmacophoric mechanisms by analyzing a plurality of molecules. More particularly, the computer begins with a set of data representing a plurality of molecules, where the data set preferably indicates for each molecule both a feature characteristic (e.g., a chemical structure and/or other features) and an activity characteristic (e.g., an observed or measured level of activity in one or more assays).

Provided with the input data set, the computer first identifies those molecules that have more than some predefined activity characteristic (level of activity), on an absolute or normalized scale. The computer then employs an agglomerative clustering technique to cluster representations of those molecules based on their structural similarity. The result of this process is a pyramidal data structure, in which each node of the structure represents one or more of the molecules.

As the pyramid is created, or after it is created, the computer preferably identifies, for each node, a feature set common to all of the molecules in the node. This common feature set may be a substructure, for instance. In that case, the computer preferably selects the largest common substructure, which is the structure most likely to explain why the molecules ended up together in the node.

In addition, for each node, the computer preferably identifies a measure of activity that is representative of the activity levels of the molecules in the node. For instance, the activity measure for a given node might be an average of the activity levels of the molecules represented by the node. This activity level may reasonably be correlated with the common substructure identified for the node, supporting a conclusion that the common substructure is, at least relatively speaking, responsible for that observed activity.

Thus, rather than merely determining how well a particular subgroup distinguishes active molecules from inactive molecules, an exemplary embodiment of the present invention can go further and determine the reason or reasons for the distinction: namely, the substructures responsible for the observed activity.

As it builds the pyramid or when it finishes building the pyramid, the processor may provide as output for viewing by an observer a description of some or all of the pyramid. By way of example, the output may take the form of a graphical depiction of the pyramid, illustrating the common substructures (e.g., chemical formulae) and representative activity levels (e.g., numerical measures, or color coding) that the processor identified per node.

Further, the processor may provide other useful output indicia. For example, the processor may provide an indication of whether the activity measure of a child node in the pyramid is greater than or less than the activity measure of its parent node and/or an indication of the extent of difference in activity. This activity differential may signify to a chemist what bearing the common substructure of the child node is likely to have with respect to the molecules of the parent node. For instance, if a given parent node gives rise to first and second children nodes, and the first child reflects an increase in average activity compared to the parent while the second child reflects a decrease in average activity compared to the parent, then a chemist can reasonably conclude that the common substructure of the first child node is likely to be a better lead (i.e., is more likely to correlate to the observed activity).

The process of agglomeratively clustering representations of molecules may generally operate as follows. First, as the base (starting level) of the pyramid, a processor forms a number of nodes (data objects, or cluster objects) in memory, each representing a respective single one of the molecules, and thus defining a singleton. Each node can thus be characterized by the structure of the molecule that it contains. (For instance, a node containing a C-N molecule can be characterized by the structure of the C-N molecule).

The processor then compares the nodes and determines which nodes are most similar to each other based on the structures of the molecules that the nodes contain. At this first level in the exemplary embodiment, this comparison is effectively a comparison of the molecules themselves, to determine which molecules are structurally most similar to each other. The processor merges those most similar nodes together into a new node, which can be characterized by the structures of the molecules that it contains. This effectively creates the next level of the pyramid, made up of the merged node and all of the remaining nodes, if any.

At the next level, the processor then repeats the comparison between nodes, merging together the most similar nodes to form another next level of the pyramid, and so forth. Ultimately, two nodes remain and are merged together to form the tip of the pyramid, which, in the exemplary embodiment, will represent the entire collection of molecules being clustered.

A problem arises at any given level of this analysis, however, when the processor encounters a tie in similarity (also referred to as a "tie in proximity") between nodes. If the processor finds that a given node A is just as similar to node B as it is to node C, then (if this is the greatest inter-node similarity at this level) a question would arise as to which nodes the processor should merge together.

Ties in similarity are most likely to occur if the molecular structures are represented by bit vectors, for instance, where each structural element can be either present or absent (1 or 0), than if features are represented by real numbers (e.g., weights). Consider three molecules x, y and z, for instance, and five structural properties a, b, c, d and e. Assume the bit vectors for these molecules are:

|   | a | b | c | d | e |
|---|---|---|---|---|---|
| x | 1 | 1 | 0 | 0 | 1 |
| y | 1 | 1 | 1 | 1 | 0 |
| z | 1 | 0 | 1 | 1 | 1 |

Molecule x includes all but structures c and d. Molecule y includes all but structure e. And molecule z includes all but structure b. Thus, molecule x differs from molecule y by 3 bits, and molecule x differs from molecule z by 3 bits as well. In this scenario, if every structural property has the same weight, then molecule x is equidistant from molecules y and z.

With a set of diverse compounds, such bit vector representations could give rise to a large number of ties in similarity. But in a more typical case, as the homogeneity of the compound set increases, the likelihood of encountering ambiguous ties when employing bit-vector representations increases even more.

One way to solve this problem is to artificially break the tie. For instance, a rule can be preset to indicate that, in response to a tie in similarity such as that described above, the choice of whether to merge A with B or C should depend on at which level in the pyramid B and C were formed. For example, if B was formed by a merger two levels ago and C was formed by a merger three levels ago, then the rule might dictate that A should be merged with C. Other such rules could be developed as well.

By breaking a tie in similarity, however, the processor will likely discard very useful information, both in terms of the merger that the processor does not select to make and in terms of further mergers that would have evolved from that non-selected merger. For instance, by opting to merge A with B rather than with C, the processor might never develop a common substructure based on a merger of A and C and therefore might never provide such potentially useful information to a chemist. Further, until very high in the pyramid, the processor might then never merge the molecules of A and C together with the molecules of another node, D. Any common substructure that could have been developed from such a subsequent merger might therefore never appear, thus depriving a chemist of possibly useful information.

The present inventors have discovered, however, that a better way to deal with a tie in similarity during the clustering process is to use the tie rather than break the tie. In particular, according to an exemplary embodiment, when the processor determines at a given level of the pyramid that substantially the same greatest similarity exists both between nodes A and B and between nodes A and C, the processor will merge A separately with both B and C, so as to form two merged nodes, A-B and A-C. Consequently, the next level of the pyramid may be made up of these two merged nodes as well as other nodes (if any) from the current level.

By merging A separately with both B and C, the processor effectively maintains, rather than discards, information. For instance, the processor may identify a common substructure respectively for each of nodes (i) A-C, (ii) A-B, (iii) A, (iv) B and (v) C. And the processor may identify a representative activity measure for each of these nodes. Advantageously, the processor may then provide this and other information (e.g., activity differential information as mentioned above) as output for use by a chemist. With the benefit of this information, a chemist may thus readily determine, for instance, that a much greater activity differential exists between parent node A-C and child node A than between parent node A-C and child node C.

In the exemplary embodiment, the present invention therefore advantageously establishes a multi-domain pyramid (or tree) structure, built from the ground up (or from the leaves to the root). Each node of the pyramid may define a pharmacophoric mechanism (e.g., substructure) and represents or comprises one or more molecules that include that mechanism. Backtracking down the pyramid (i.e., opposite the direction that the pyramid was built), each parent node may lead to one or more children nodes, each preferably defining a further pharmacophoric mechanism, and each including those molecule(s) from its parent node that include the mechanism.

According to the exemplary embodiment, the processor may further trim the pyramid (i.e., the tree), to remove nodes that are not particularly useful. For instance, if the processor determines that the common substructure identified for a given node is the same as that of its parent node, then the processor can remove the child node from the pyramid and change the output to reflect that any children of the child node are instead children of the parent node. As another example, the processor can be programmed to remove all nodes from the base layer of the pyramid, since each of those nodes in the exemplary embodiment represents a single molecule, which is not particularly useful information for a chemist.

A pyramid structure produced in accordance with an exemplary embodiment of the invention can represent, in and of itself, a large amount of commercially valuable information, much of which was previously out of reach. As an example, for each node of the pyramid (after the root node), the common substructure (pharmacophoric mechanism) identified for the node can be commercially valuable information, since it represents a substructure that is likely to be responsible for observed pharmacophoric activity. Such a substructure might therefore be usefully employed to develop beneficial new drugs.

As another example, any lineage of nodes in the pyramid (e.g., from a given node up or down to another node) can embody a significant amount of commercially valuable information. By the time one or more molecules reaches a terminal node (i.e., the base) of the pyramid, for instance, the molecule(s) may have passed through a number of nodes defining their ancestral parent node(s), each having a respective common pharmacophore. This ancestral line of pharmacophores may therefore represent the pharmacophoric mechanisms that, cooperatively, are likely to result in an activity level reflected by the molecule(s) in the terminal node.

As yet another example, as noted above, the difference in activity levels between molecules in a child node and molecules in its parent node can be very valuable information, since the difference may represent the enhancing or detracting effect of the pharmacophoric mechanism that gave rise to the child node. Such information is even more valuable when a given parent node gives rise to a pair of children nodes and the activity differential varies greatly among the children nodes. For instance, if one child node reflects an activity increase compared to the parent, while the other child node reflects an activity decrease compared to the parent, it is reasonable to conclude that the pharmacophoric mechanism defined by the one child node is likely to be more useful for development of beneficial new drugs.

An exemplary embodiment of the present invention can thus take a massive amount of data representing chemical compounds and convert that data into a pyramid structure that conveniently and intuitively represents the foregoing and other valuable information. A chemist, who could not manually analyze such a vast amount of input data, can then readily analyze the organized information represented by the pyramid structure. The information generated by the invention can thus assist in the development of leads and in turn the development of beneficial new drugs.

Thus, in one respect, an embodiment of the invention can take the form of a method for identifying chemical substructures by analysis of a data set representing a plurality of chemical structures. The method can include executing a computer program to pyramidally cluster representations of the chemical structures, so as to produce in a data storage medium a hierarchy of clusters, where each cluster represents one or more of the chemical structures. This process can include comparing clusters and merging together pairs of clusters that have the greatest similarity. In this regard, the process can include finding, at a given level of the hierarchy, that at least two pairs of clusters have substantially the same similarity, and then responsively merging each pair respectively, so as to form at least two new clusters at the next level of the hierarchy.

Further, the process of executing a computer program to pyramidally cluster the molecular representations can involve applying a clustering algorithm. The identity of the clustering algorithm (i.e., the particular algorithm—such as Wards, complete-link, or the like) can be specified by a user, and a computer may execute the specified algorithm. Further, a user may specify one or more other aspects of the clustering algorithm, such as, for instance, a fuzziness parameter that indicates how strict or lenient the computer will be when deciding whether a tie in similarity exists between two pairs of clusters. As an example, the fuzziness parameter could indicate a range of similarities that could be considered ties.

With respect to each of the clusters of the hierarchy, the method can further include analyzing the chemical structure (s) in the cluster and determining a chemical substructure that is representative of the chemical structure(s) in the cluster. In turn, the method can include outputting for consideration by a person a description of at least a portion of the hierarchy and an indication of at least one of the representative chemical substructures.

In another respect, an embodiment of the invention can take the form of a method of identifying pharmacophoric mechanisms through analysis of a plurality of molecules, where each molecule has a respective feature characteristic and a respective activity characteristic. The method can involve establishing in a computer memory a plurality of cluster objects, each representing one of the molecules, and then agglomeratively clustering the cluster objects based on comparisons of the feature characteristics of the molecules that the cluster objects represent. In this process of agglomeratively clustering, to the extent any given cluster object is determined to be equidistant to a plurality of other cluster objects, the method may further include merging the given cluster object with each cluster object of the plurality of other cluster objects. In any event, the result can be, in a computer memory (or, equivalently, another type of data storage medium), a hierarchical pyramid made up of a number of cluster objects each representing a number of the molecules.

With respect to each of at least some cluster objects of the pyramid, the method may further include identifying a substructure that is common to molecules represented the cluster object. Such a substructure may define a respective pharmacophoric mechanism. In turn, the method may include outputting for viewing by a person a description of at least part of the hierarchical pyramid, including at least one of the identified substructures.

In yet another respect, an embodiment of the invention can take the form of a method of identifying pharmacophoric mechanisms through analysis of a plurality of molecules, where each molecule defines a feature characteristic and an activity characteristic. The method can include establishing in a computer memory a plurality of data objects, each representing one of the molecules and having associated with it a feature vector that represents the feature characteristic of the molecule.

In turn, the method can include pyramidally clustering the data objects based on their associated feature vectors, so as to form in the computer memory a pyramidal data structure having a number of nodes each representing one or more of the molecules. In the process of pyramidally clustering the data objects, the method preferably includes encountering a tie in proximity between a given node and at least two other nodes and responsively merging the given node separately with each of the at least two other nodes.

The method may further include, with respect to each node of the pyramidal data structure, identifying a chemical feature set common to the one or more molecules represented by the node. This chemical feature set can be considered to define a pharmacophore. Still further, the method can include providing an output that describes (or, equivalently, otherwise indicates) at least a portion of the pyramidal data structure and that includes a description of the chemical feature set identified with respect to at least one node of the pyramidal data structure.

In another respect, an embodiment of the invention could take the form of a method of learning pharmacophoric mechanisms through analysis of a plurality of molecules, each having a respective feature characteristic and a respective activity characteristic. This embodiment of the invention could involve selecting from the plurality of molecules a group of molecules that has at least a threshold activity characteristic (i.e., in an exemplary embodiment, each molecule of the group having at least the threshold activity characteristic—such as a threshold level of activity, for instance). Further, the method could involve establishing in a data storage medium a plurality of data objects that each represent at least one of the molecules of the group, such that at least one of the data objects (object 1) represents two or more molecules. Establishing these data objects in memory can itself involve developing a representation of each molecule and then agglomeratively clustering the representations into a hierarchy, where object 1 resides at a given level.

The invention may then- involve measuring similarity between the data objects based on the feature characteristics of the molecules represented by the data objects. Based on these measurements, the invention could involve making a determination that the similarity between object 1 and another data object (object 2) is substantially equal to the similarity between object 1 and still another data object (object 3). In response to that determination, the method could involve merging object 1 separately with object 2 to form a new data object (object 4) and with object 3 to form a new data object (object 5).

The method may then involve identifying at least (i) a common feature set among the feature characteristics of the molecules represented by object 1 and (ii) a common feature set among the feature characteristics of the molecules represented by object 4. Each of these common feature sets can be considered to define a respective pharmacophoric mechanism.

The method may further include providing to a person an indication of at least the common feature sets identified with respect to the molecules of objects 1 and 4. In conjunction with this output, the method could include computing representative activity levels of each object as well as a differential between the activity levels of at least objects 1 and 4, and possibly providing an indication of the differential. A person may then correlate the differential with the common feature set identified with respect to object 1.

The method may additionally include representing each feature characteristic as a binary vector whose members indicate the presence or absence of respective molecular features. (The process of so representing the feature characteristic may involve generating the binary vectors, or simply receiving the vectors as input.) With this arrangement, the process of measuring similarity between data objects can involve evaluating (i.e., measuring or computing) similarity between respective pairs the data objects based on the binary vectors of the molecules represented by the data objects of the pair. As between any two data objects, this similarity computation can involve computing a Tanimoto distance, a Euclidean distance, or other distance measure between the data objects.

In still another respect, an embodiment of the invention could take the form of a method for analyzing a plurality of molecules, each of which having a respective feature characteristic and a respective activity characteristic. The respective activity characteristic of each molecule preferably represents at least a threshold activity level. The method can then include establishing in a computer memory a plurality of cluster objects, each cluster object representing at least one of the molecules.

With respect to the cluster objects, the method can involve conducting a merging process that includes (i) comparing pairs of the cluster objects and, for each pair, measuring a respective dissimilarity between the cluster objects within the pair based on the feature characteristics of the molecules represented by the respective cluster objects, (ii) of the dissimilarities measured in step (i), identifying a smallest dissimilarity, (iii) selecting at least one pair of the cluster objects that has the smallest measured dissimilarity, and (iv) with respect to each of the at least one pair selected in step (iii), merging the cluster objects of the pair to establish a cluster object cooperatively representing the molecules that were represented by the cluster objects of the pair. With respect to at least each cluster object established in step (iv), the method can further include identifying a common substructure among the molecules represented by the cluster object.

At each level of merger, if at least two cluster objects have not yet been merged, the method can involve conducting the merging process again, but with respect to the cluster objects that have not yet been merged.

Further, the method can include outputting a description of at least one of the established cluster objects, including at least an indication of the common substructure identified for that cluster object. This output can include a graphical description (such as a tree structure) of cluster a objects, including for each cluster object an indication of the common substructure established with respect to the cluster object. Alternatively or additionally, a graphical depiction can include for each cluster object an indication of a measure of the activity characteristics of the molecules represented by the cluster object, and/or perhaps a measure of activity differential between parent and child clusters in the pyramid.

In yet another respect, an embodiment of the present invention can take the form of a processing system for screening a data set representing a plurality of molecules, so as to assist in identifying sets of molecular features that are likely to correlate with specified activity. The data set may define, for each represented molecule, a feature characteristic and an activity characteristic. And the processing system may include a processor, at least one data storage medium, and a set of machine language instructions stored in the data storage medium and executable by the processor to perform functions such as those described above.

In a further respect, an embodiment can take the form of a set of a computer-readable medium (such as a memory, a magnetic or optical disk, or a tape, for instance) that embodies a set of machine languages instructions executable by a computer for performing method steps such as those described above or such as those depicted in the accompanying figures.

In yet a further aspect, an exemplary embodiment of the present invention involves applying a pyramid structure generated in accordance with the invention in order to classify other compounds, so as to "virtually" determine what level of activity might be expected of a known or unknown molecule.

The foregoing as well as other advantages and features of the present invention will be understood by those of ordinary skill in the art by reading the following detailed description with reference where appropriate to the accompanying drawings.

BRIEF DESCRIPTION OF THE DRAWINGS

An exemplary embodiment of the present invention is described herein with reference to the drawings, in which:

FIGS. 3a, 3b, 3c and 3d are table listings of illustrative set of descriptors for use in an exemplary embodiment of the invention;

DETAILED DESCRIPTION OF AN EXEMPLARY EMBODIMENT

As indicated above, the present invention provides a computer-based system for the automated analysis of a data set. The system is configured to correlate features with responses and to thereby identify or discover scientifically useful subclasses of features or mechanism models, namely, features that are likely to correspond to observed or predicted responses.

An exemplary embodiment of the invention provides a computer-based system for generating structural subclasses that relate to pharmacophoric activity and thereby generating a pyramid structure that embodies rules or processes for creating (i.e., identifying or establishing) scientifically useful pharmacophoric mechanisms.

The functional steps described herein are preferably encoded in a set of machine language instructions (e.g., source code compiled into object code), which are stored in a computer memory or other storage medium (e.g., a computer disk or tape) and executed by a general purpose computer. (Alternatively, the functional steps may be carried out by appropriately configured analog or digital circuitry, or by any combination of hardware, software and firmware.)

The present invention may thus take the form of a computer-based system, which itself may comprise, for example, (i) a method for performing a plurality of functional steps, (ii) a computer readable medium (such as a disk, tape or other storage device) containing a set of encoded machine language instructions executable by a computer processor for performing a plurality of functional steps, and/or (iii) a machine (such as a general purpose digital computer) programmed with a set of machine language instructions for carrying out a plurality of functional steps (in the recited order or in a varied order).

Provided with this disclosure, those of ordinary skill in the art will be able to readily prepare a suitable set of instructions for performing these functions and to configure a general purpose computer to operate the instructions. Such instructions would likely be compiled into a set of machine-language (machine-readable) instructions, which would then be stored in a data storage medium (such as a memory) and executed by a processor.

1. Overview

An exemplary embodiment of the present invention provides a computer-based system for generating pharmacophoric subclasses through multi-domain agglomerative clustering and for thereby generating pyramid structures that embody subclass definitions (e.g., common substructures) correlated with observed or predicted activity. More particularly, an exemplary embodiment will be described in the context of chemical SAR analysis and the development of pyramid structures representing pharmacophoric mechanism models.

Figure 1:
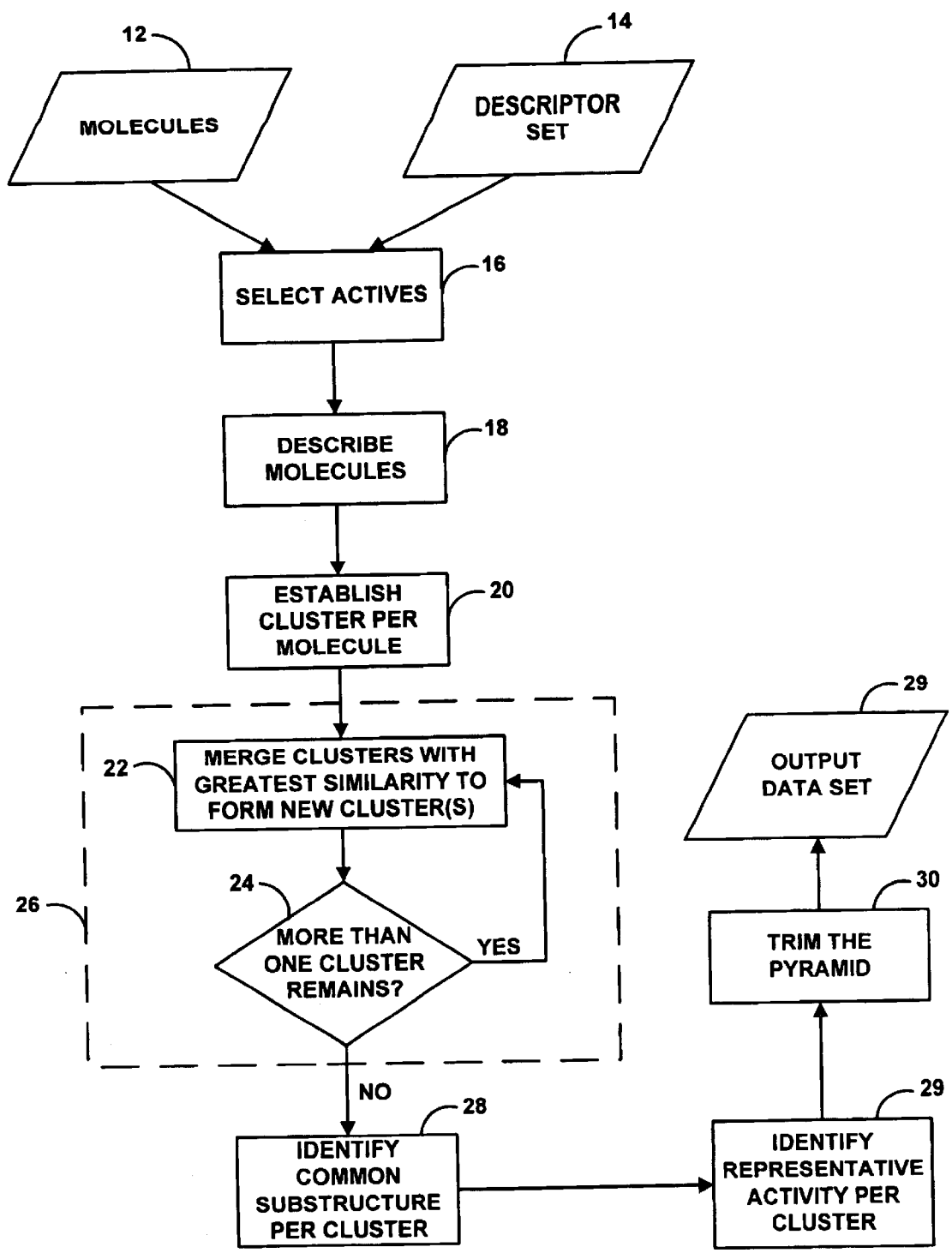
FIG. 1 is a flow chart illustrating an exemplary set of functions that a computer performs according to an exemplary embodiment of the invention.

Referring to the drawings, FIG. 1 is a flow chart illustrating an exemplary set of functions that a computer may perform according to an embodiment of the present invention. An overview of these functions will first be provided, and each function will then be described in more depth so as to enable one of ordinary skill in the art to practice the invention as presently contemplated. It will be appreciated that a computer-system may be readily programmed to execute an appropriate set of machine languages instructions designed to carry out some or all of these functions as well as other functions if desired. Further, it should be appreciated that variations to the routines described herein, and to the order of the routines, are possible.

As shown in FIG. 1, at block 12, the computer may receive or be programmed with a set of digital data representing molecules and their respective activity levels. The activity level of each data object may be one dimensional or multi-dimensional.

At block 14, the computer may also receive or be programmed with a set of digital data representing an initial set of descriptors or "keys" that may define a particular pattern (subgraph) in a molecule (graph). These patterns preferably relate to physical chemical properties such as atoms, bonds, shapes, sizes, etc. (hereafter referred to generally as "structure"). Therefore, these keys may alternatively be referred to as "substructure keys", "substructure descriptors" or the like. If desired, each of these keys may be weighted to indicate the relative importance of the keys, as defined by an expert and/or through computer analysis for instance. The data sets referenced at blocks 12 and 14 may alternatively be a single data set.

At block 16, the computer may select from the molecules of the input data set those molecules that have at least some predefined relative level of activity (on a normalized scale that considers the activity levels of all of the molecules represented by the input data set). The computer may then continue its processing with respect to these "active" molecules, leaving the other "inactive" molecules for later analysis if desired.

At block 18, the computer may establish a description for each molecule, based on a comparison of the features of the object with the set of keys. The description for each object may take any desired form. The description for each object may take the form of a descriptor vector (e.g., bit string), each element of which may be a binary indication of whether a corresponding one of the keys in the key set is present or absent in the molecule. Each descriptor vector may thus be the length of the key set. Alternatively, it is appreciated that the description may indicate expressly only which descriptors are present, thus implicitly indicating the absence of other descriptors. Further alternatively, rather than having the computer generate a description for each molecule, the input data set may instead include pre-established descriptions for each molecule.

At block 20, the computer may then establish in memory a cluster object (equivalently, "cluster", "node", or "data object") corresponding respectively to each molecule. These singleton is clusters cooperatively define a base (first) level of the pyramid that will be established by the computer. The computer may characterize each cluster by a descriptor vector that is based on the descriptor vector of the molecule that the cluster contains (represents). Thus, at this first level of the pyramid, each cluster may have a descriptor vector equal to the one molecule that it contains.

At block 22, the computer then engages in a merging process. The computer compares pairs of the clusters and, for each pair, determines a similarity measurement between the clusters within the pair. Of all of the similarity measures thus determined, the computer then identifies the greatest similarity. (Equivalently, for purposes of this specification, this process may be described as the computer determining a dissimilarity measure between clusters and then identifying the least dissimilarity. It should be understood that this is merely a matter of terminology and perspective.)

With respect to each pair of clusters that has this greatest similarity (or, equivalently, the least dissimilarity), the computer then merges the clusters of the pair together to form a new cluster. Similar to the singleton clusters, the computer may characterize each such merged cluster by a descriptor vector that is based on the descriptor vectors of the molecules that the cluster contains. Any of a variety of mechanisms can be employed for this purpose. For instance, the characteristic of the cluster can be an average of the descriptor vectors of the molecules that the cluster contains.

It is possible that only one pair of the clusters might have the greatest similarity. In that case, the computer in the exemplary embodiment would merge the clusters of that pair into a new cluster. For instance, if clusters A and B are the most similar, then the computer would merge cluster A and B together to form a new cluster AB. Cluster AB will contain the molecules that were cooperatively contained in nodes A and B.

It is also possible, however, that two of more of the pairs of clusters might all have the greatest similarity. This may occur when the similarities computed for the multiple pairs are identical (equal), or when they are substantially identical. Of course, the determination of what would constitute "substantially" identical is a matter of choice, and will usually be made by user input to the computer or otherwise predefined. Faced with multiple pairs having the greatest similarity, the computer in the exemplary embodiment will separately merge the clusters of each pair together to form a new merged cluster based on each pair.

If multiple pairs have the greatest similarity, and those pairs share a common cluster, then a tie in similarity (or "ambiguous tie") has occurred. For instance, if cluster A is equidistant (in a statistical comparison sense) from clusters B and C, and the distance between cluster A and each of these other clusters is the smallest distance among the pairs under analysis, then the computer would merge A with B to form one new cluster AB, and the computer would merge A with C to form another new cluster AC. Cluster AB will contain (represent) the molecules that were cooperatively contained in nodes A and B, and cluster AC will contain the molecules that were cooperatively contained in nodes A and C.

It is also possible that there may be more than two pairs involved in a tie. For example, a given node A might be equidistant from nodes B, C and D. If its distance from each of these nodes is the smallest distance (the greatest similarity), then the computer may merge (i) A with B, (ii) A with C and (iii) A with D.

The computer has then reached a new level of the pyramid, which, in the exemplary embodiment, is made up of the new merged cluster(s) together with any other clusters that were not just merged.

At block 24, the computer then determines whether more than one cluster remains. If so, the computer has not yet reached the tip of the pyramid. Therefore, the computer iteratively repeats the process, returning to block 22, searching for a greatest similarity between pairs of clusters at the new level of the pyramid: Blocks 22 and 24, cooperatively, represent the pyramidal agglomerative clustering process, designated in FIG. 1 by reference numeral 26.

At any given level of the pyramid after the first (in the exemplary embodiment), at least one of the comparisons (of clusters within a pair) made by the computer will be a comparison between a multi-molecule cluster (e.g., one that itself resulted from a merger of other clusters) and another cluster. Numerous statistical techniques are available to make this comparison. By way of example, the well known Wards agglomerative clustering method formula may be used to make the comparison. However, in addition to Wards, other methods for comparing a multi-member cluster to another cluster include complete-link, group average link, single link and centroid method, each of which is known in the art. Any of these or other comparison techniques can be used if desired.

In an exemplary embodiment, for instance, the comparison between a non-singleton cluster and another cluster can be done at least in part by evaluating distances between the a molecules in the respective clusters. For example, the distance between clusters A and B can be defined by the maximum pairwise dissimilarity (or minimum pairwise similarity) of the molecules that clusters A and B contain. Thus, if cluster A contains molecules 1 and 2, and cluster B contains molecules 3 and 4, distances can be measured, respectively, for molecule pairs 1-3, 1-4, 2-3 and 2-4. Of these distances, if molecule pair 1-3 has the maximum distance (or minimum similarity), then, according to the complete-link clustering technique, the distance between molecules 1 and 3 can be selected to define the distance between clusters A and B. Phrased differently, the most similar cluster-pair of a set of clusters available to be merged can be the cluster-pair whose maximum pairwise dissimilarity is the minimum of all possible pairs of clusters under investigation.

At block 28 (which could alternatively be done in parallel with the other blocks, e.g., by a parallel processor), the computer analyzes and identifies at least one largest common substructure (or other significant common substructure)

among the molecules represented by each cluster. As desired, this common substructure may be a contiguous or non-contiguous arrangement of atoms and bonds, for instance, or could take other forms (whether 2D or 3D in nature). This common substructure is most likely to be responsible for the similarity of the molecules in the cluster, i.e., the reason why the molecules ended up in the given cluster.

In addition, at block 29, the computer computes a representative activity level for each cluster. For a singleton cluster, the activity level should be the activity level of the one molecule represented by the cluster, but the computed activity could take other forms. For non-singleton clusters, any desired mechanism can be employed to compute the representative activity level. For instance, the activity level could be an average of the activity levels of the molecules represented by the cluster.

At block 30, the computer may then trim the pyramid, removing from the pyramid any clusters that the computer determines to not reflect sufficiently useful information. As examples, the computer could remove all singleton clusters (i.e., those that formed the base of the pyramid), and the computer could remove each child cluster that has the same identified common substructure as its parent (the next cluster higher in the pyramid).

At block 32, the computer then provides an output, for presentation to a chemist or other person, or for use in another stage of analysis. The output could take a variety of forms but preferably represents structural families of compounds and SAR information.

The output may be a description of all or part of the pyramid structure. For example, the output can be a graphical or text or data based description of the various clusters and links between nodes (e.g., links showing child-parent relationships). For each node, the output can indicate the common molecular substructure and representative activity level identified by the computer. As another example, the output may indicate activity differentials reflecting a change in representative activity level from a parent cluster down to each of its child clusters.

Figure 2:
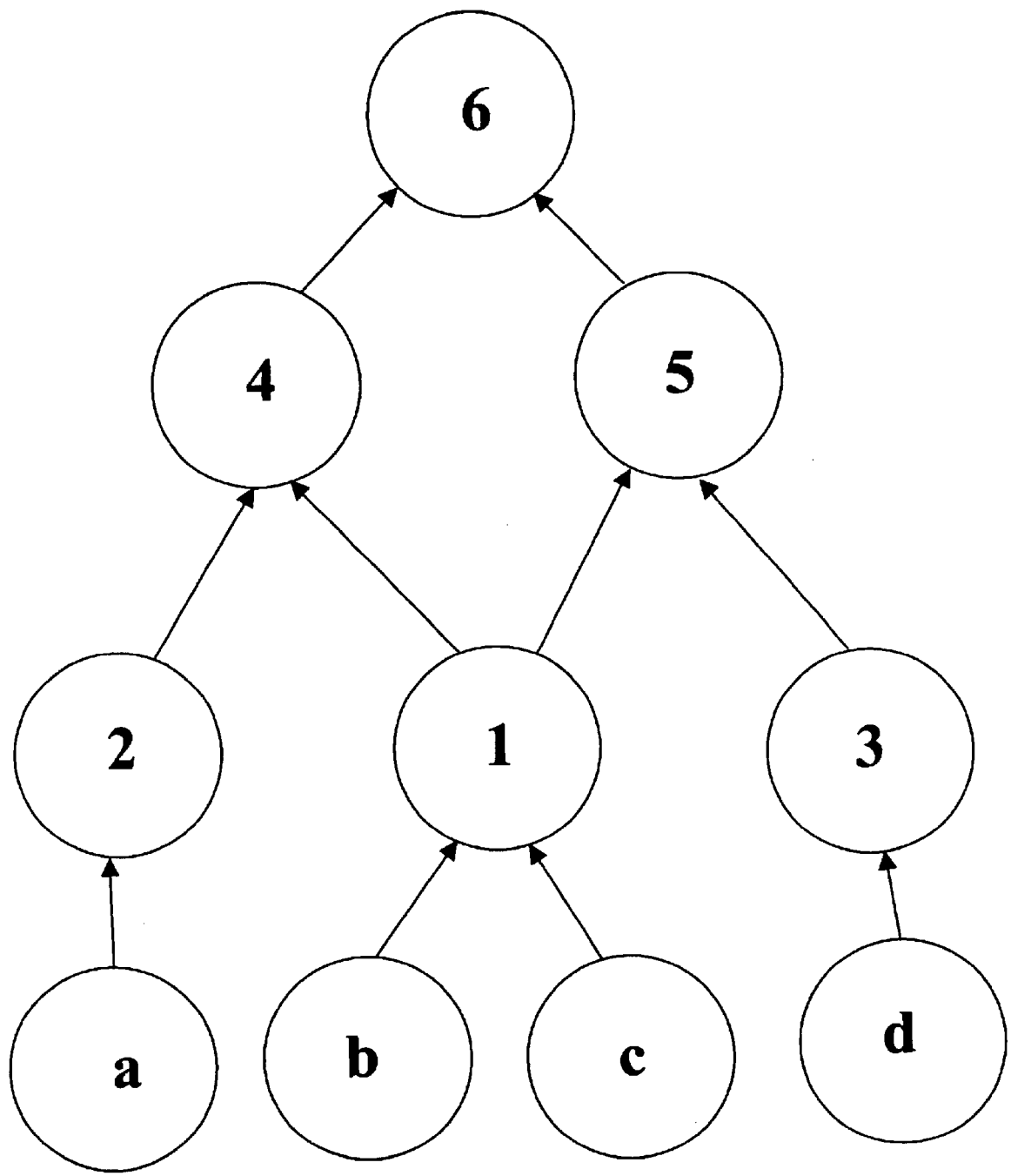
FIG. 2 a simplified block diagram illustrating the creation of a pyramid in accordance with an exemplary embodiment of the invention.

FIG. 2 a simplified block diagram illustrating the creation of a pyramid in accordance with an exemplary embodiment of the invention. The simplified example of FIG. 2 assumes that the input data set represents four molecules, a, b, c and d, that have been determined to be active. (The input data set might have been only these molecules or might have been a larger set of these and other molecules.) In a computer memory, clusters a, b, c and d respectively represent these four molecules and cooperatively form the base of a logical pyramid.

The computer then measures similarity between clusters in pairs of these clusters, preferably measuring the similarity for every possible pair, a-b, a-c, a-d, b-c, b-d and c-d. In this simplified example, assume the computer determines that clusters b and c are the closest together. Thus, the computer merges clusters b and c together to make a new cluster 1. Consequently, at the next level of the pyramid, there are three nodes, 1, 2 and 3, as follows:

Cluster 1: Representing molecules b and c
Cluster 2: Representing molecule a
Cluster 3: Representing molecule d At this next level, the computer measures similarity between clusters in pairs of the clusters, again preferably measuring the similarity for every possible pair, 1-2, 1-3 and 2-3. Assume in this example that the computer determines that the greatest similarity exists between both clusters 1 and 2 and clusters 1 and 3, thus presenting a tie in similarity. Consequently, the computer merges cluster 1 with cluster 2 to make a new cluster 4, and the computer also merges 1 with cluster 3 to make a new cluster 5. This gives rise to the next level of the pyramid, where clusters 4 and 5 are as follows:

Cluster 4: Representing molecules a, b and c
Cluster 5: Representing molecules b, c and d At this next level, the computer again measures similarity between clusters in pairs. Because only one pair, 4-5, exists, the computer merges clusters 4 and 5 together to form the final cluster 6 as the tip of the pyramid. Cluster 6 represents all of the molecules, a, b, c and d, that were agglomeratively clustered.

In the exemplary embodiment, the computer then (or as the building-process occurs) identifies for each cluster (i) a largest common substructure and (ii) a representative activity level. The computer then provides as output a description of the resulting pyramid structure.

2. Functional Blocks a. Receiving Data

According to an exemplary embodiment, the computer preferably receives or is programmed with a data set representing molecules and their respective activity levels (i.e., potencies or responses). This data set may result from combinatorial chemistry and/or high throughput screening techniques, or from any other source.

Each molecule is preferably represented by an ASCII string or any other suitable representation that can be computer processed. (Any data string representing a molecule may be referred to as a "molecule data string.") By way of example and without limitation, a useful system for representing chemical molecules in ASCII form is provided by Daylight Chemical Information Systems, Inc., of Irvine, Calif. Daylight establishes a language that it terms "SMILES" (Simplified Molecular Input Line Entry System), which contains the same information about a molecule that would be found in an extended connection table but sets forth the molecule as a linguistic construct rather than as a data structure. Examples of SMILES strings include:

| | |
|---|---|
| ethane: | CC |
| carbon dioxide: | O=C=O |
| hydrogen cyanide: | C#N |
| riethylamine: | CCN(CC)CC |
| acetic acid: | CC(=O)O |
| cyclohexane: | ClCCCCCl |
| benzene: | clccccc1 |

A unique molecule may be represented by more than one SMILES string. For example, $N^2$isopropyl benzoylhydrazide may be represented by both the string "c1ccccc1C (=O)NNC(C)C" and the string "CC(C)NNC(c1ccccc1) =O". The Daylight program therefore generates a connection table, which maps the exact structure of each molecule, in terms of atoms and their bond connections, from various possible representations of the molecule.

As indicated by Daylight, SMILES strings provide a compact, human understandable and machine readable representation of molecules, which can be used for artificial intelligence or expert systems in chemistry. Other information about the creation and use of SMILES strings is readily accessible at Daylight's world wide web site, which is located at http://www.daylight.com, and the reader is directed to the Daylight web site for more detailed information. In addition, further information about SMILES strings is provided in the Journal of Chemical Information and Computer Science, 1988, 28, 31–36.

The molecule representations may be provided in the same or a separate data set as the activity information. For example, a single data file or database may contain separate entries or records for each molecule, including as separate fields (i) a bit string molecule identifier and (ii) a bit string activity identifier. Alternatively, separate data files or databases (or separate tables) may be provided for the molecules and for empirical data gathered with respect to the molecules in one or more assays. In a preferred embodiment, each molecule will be represented by a unique molecule ID (e.g., a database record number), for convenient reference.

The activity information for a molecule may take any suitable form. By way of example and without limitation, the activity information may be an absolute measure of activity of the molecule in an assay or may be a measure of activity relative to the average activity of all molecules tested in an assay. For instance, a molecule may be tested at various levels of concentration, a curve fit to the concentration vs. activity points, and the concentration necessary to cause half of the maximum activity determined. The activity information for the molecule may then be the resulting $IC_{50}$ concentration.

Further, the activity information for a molecule may be one-dimensional or multi-dimensional. For instance, the activity may be a single measurement of whether or how well the molecule bound to a particular protein in an assay. This measurement may be indicated, for instance, by an integer (such as a rank between 0 and 3, where 0 indicates inactivity and 3 indicates the highest relative level of activity) or by a Boolean value (where "true" indicates activity and "false" indicates inactivity). Alternatively, the activity may be multi-dimensional, such as an indication of how the molecule performed in various aspects of a single assay or multiple assays. Such multi-dimensional activity information for a molecule may be represented by a vector, for instance, whose members indicate activity levels of the molecule for a plurality of assays. In any event, the activity information for each molecule is preferably encoded in a format suitable for computer processing, such as in a bit string.

In addition, the computer preferably receives or is programmed with a set of substructure descriptors keys, which can serve to represent aspects of chemical molecules. Each key may be any property that can define a physical aspect of a chemical molecule. By way of example and without limitation, the keys may specify atoms, atom pairs, proton donor-acceptor pairs, other groupings, aromatic rings, characteristics of atoms or sets of atoms (e.g., hydrogen bond affinity, location of electron density, etc.), shapes, sizes and/or orientations. Further, the keys may define 2-D representations (such as atom pairs, bonds and aromatic rings, for example) or 3-D representations (such as a distance between chemical components having variable orientation, and an indication of component orientation, for example) or both.

Each substructure key may be weighted to indicate the relative importance of the key in describing two molecules that are similar. By way of example, these weights may be pre-established (e.g., by a chemist) based on a statistical measurement of how "unusual" it is to find the substructure in a population of molecules; the more unusual the substructure, the more similar are molecules that share the substructure, and so the more highly weighted the key. Alternatively, keys may not be weighted, or may equivalently each be assigned a weight of 1.

Each substructure key is preferably represented by an ASCII string or any other suitable representation that can be computer processed. (Any data string that represents a descriptor may be referred to as a "descriptor data string.") By way of example and without limitation, a useful system for representing chemical molecules in ASCII form is also provided by Daylight Chemical Information Systems, Inc. Daylight establishes a language called "SMARTS," which can be used to specify substructures using rules that are straightforward extensions of SMILES strings. Additional information about Daylight SMARTS keys is provided at the Daylight web site indicated above.

According to Daylight, both SMILES and SMARTS strings employ atoms and bonds as fundamental symbols, which can be used to specify the nodes and edges of a molecule's graph and assign labels to the components of the graph. SMARTS strings are interpreted as patterns that can be matched against SMILES string representations of molecules, in the form of database queries for instance. Other examples of substructure representations include "MACCS" keys (i.e., fragment-based keys for use in describing molecules, where MACCS stands for "the Molecular ACCess System) and other keys as defined by MDL Information Systems, Inc., for instance. (For additional information about the keys established by MDL, the reader is directed to MDL's web site, at http://www.mdli.com.) For 3-D substructure keys, still other sorts of representations might be employed.

The set of substructure keys may be of any desired size, and the keys may take any desired form. In an exemplary embodiment, however, the computer uses a set of keys specified in the SMARTS language to emulate 157 of the MACCS keys defined by MDL, which have been selected to provide structural descriptions of molecules and to thereby facilitate improved correlation of structure and activity. FIG. 3 provides a table of these 157 keys as SMARTS string representations and lists for each key an optional weight and a corresponding MDL MACCS definition. Of course, it will be appreciated that other key definitions and forms of keys can be used instead, depending on the features of interest being studied for instance.

b. Selecting Actives

A training set of molecules is preferably used to build the pyramid structure. This training set could be all or a subset of the molecules represented by the input data set. In an exemplary embodiment, however, the training set is all of the active molecules in the input data set, and none of the inactive molecules.

A molecule may be deemed to be active for this purpose according to any desired criteria. By way of example, a molecule may be deemed to be active if its activity level exceeds some predetermined level or is non-zero. As another example, if the activity characteristic of each molecule is multi-dimensional, then a molecule may be deemed to be active if the molecule is active with respect to each of a set of assays (various dimensions of the activity characteristic). In other words, a molecule may be deemed to be active if the molecule has some desired set of activity characteristics in a multi-dimensional representation of active (for example, active along all dimensions or active along some dimensions and inactive along others, etc).

This training set of active molecules advantageously enables the computer to learn what makes the active molecules similar to each other. The inactive molecules could then be used subsequently for testing. Alternatively, the training set can be a subset (sample) of the active molecules, and the remaining active molecules could be used subsequently for testing. Still a alternatively, any other training set can be used.

C. Establishing Descriptor-Vectors

The computer preferably establishes a description of each molecule based on the set of substructure keys. In an exemplary embodiment (i.e., without limitation), the description for each molecule may take the form of a descriptor-vector, whose elements indicate whether respective keys in the substructure key set are present or absent in the molecule (i.e., whether the respective substructures are present or absent in the molecule). If the molecules are represented by SMILES strings and the keys are represented by SMARTS strings, the computer can readily determine whether a key is present in a molecule by querying the corresponding SMARTS string against the corresponding SMILES string (and more particularly the Daylight connection table).

The members of the descriptor vector for a molecule may be values reflecting the weights of the keys that are present in the molecule. By way of example, for each key that is present in a molecule, the corresponding member of the descriptor vector for the molecule may be the weight of the key, and, for each key that is absent, the corresponding member of the descriptor vector may be zero. For instance, if a key has a weight of 5 and the computer deems the key to be present in a molecule, then the computer may assign a value of 5 to the corresponding element of the descriptor vector for the molecule. On the other hand, if the computer deems the key to be absent from the molecule, then the computer may assign a value of 0 to the corresponding vector element.

Alternatively or additionally, as in the exemplary embodiment, each member of the descriptor vector for a molecule may simply reflect the presence or absence of the key in the molecule. In this regard, the value of each member of the descriptor vector may be a binary weight (e.g., 0 or 1), and the descriptor vector may take the form of a simple bit string. This arrangement is most useful in a situation where the descriptors themselves are not weighted. Further, this arrangement can be useful in a situation where the computer maintains the weights of the keys in a separate file or table, for instance, so that the weights are associated by reference with the respective (non-zero) elements of each descriptor vector.

In an exemplary embodiment, the computer may require each key to appear at least a predetermined number of times in the molecule at issue in order for the key to be deemed "present" in the molecule. The predetermined number of times is a matter of design choice and may vary per key. By way of example, column 2 of FIG. 3 lists for each key a minimum number of hits that can be required in order to deem the respective key to be present in a molecule. Referring to this column for instance, exemplary key 134 is shown to have a minimum number of hits of 2 (for example), so the computer should find at least two nitrogen atoms in a molecule in order to deem the key to be present in the molecule. Of course, other values can be used instead.

Figure 4:
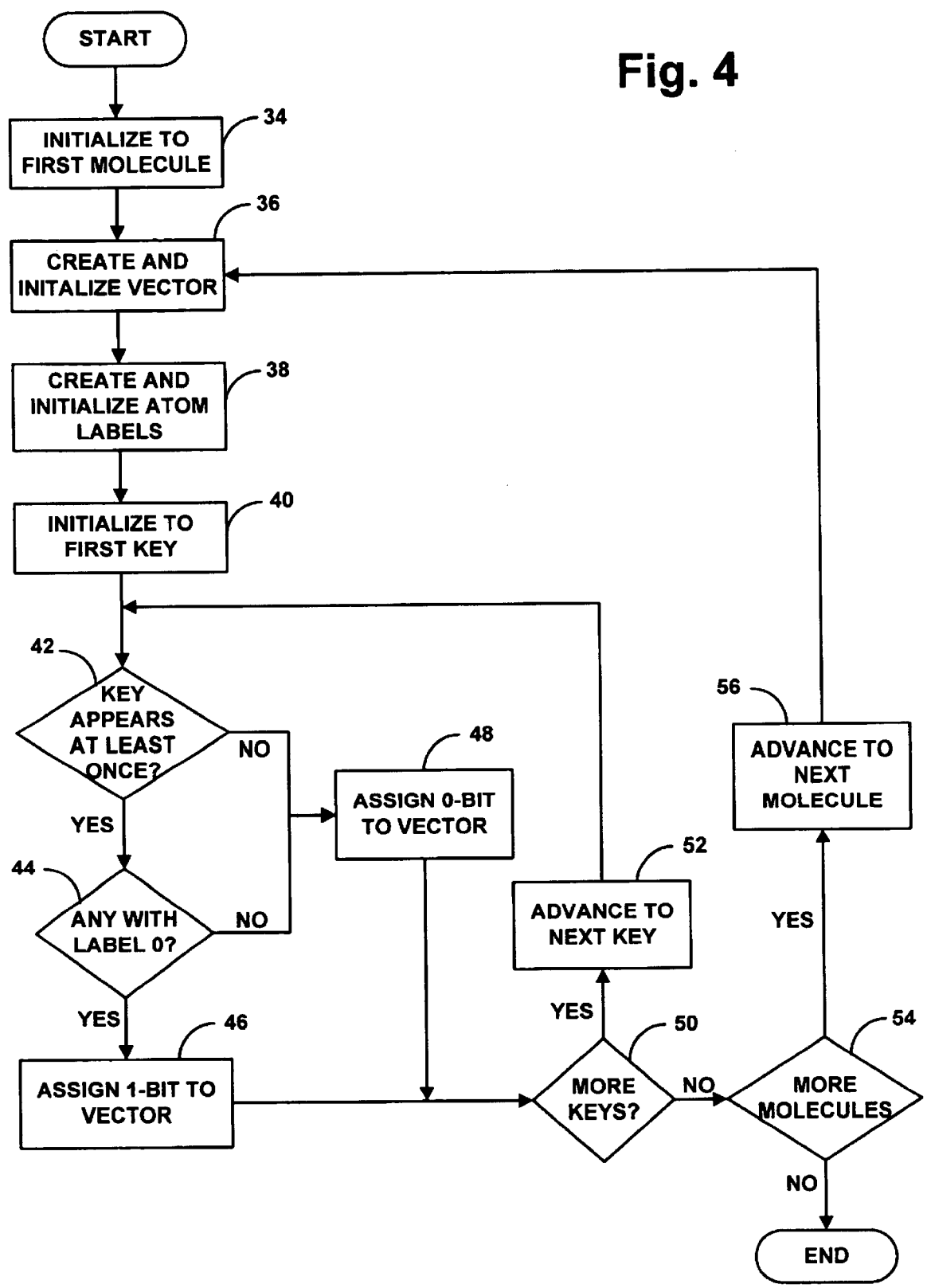
FIG. 4 is a flow chart illustrating an exemplary set of functions that a computer performs to generate descriptor vectors according to an exemplary embodiment of the invention.

Referring to the drawings, FIG. 4 illustrates an exemplary set of functional blocks that may be involved in establishing descriptor-vectors. In this example, at block 34, the computer may initialize a pointer (e.g., counter) to the first molecule (SMILES string). For the given molecule, at block 36, the computer may create a descriptor vector of a length corresponding to the number of keys (157 in the present example), and initialize each member of the vector to zero. In addition, at block 38, the computer may establish a label for each component (e.g., each atom) in the molecule, which the computer will subsequently use to indicate whether the atom has participated in matching a substructure key, and in turn to determine whether a key is wholly subsumed in the molecule by another key. The computer may initialize the label for each component to a value of zero, indicating that the component has not yet participated in matching a substructure key.

At block 40, the computer may then initialize a pointer to the first substructure key (SMARTS string). At block 42, the computer may then search the connection table associated with the SMILES depiction of the molecule to determine whether the key appears at least once (or, alternatively, at least a designated minimum number of times) in the molecule. If so, then, at block 44, the computer may determine whether at least one component (e.g., atom) in the molecule that participated in matching the key has a label set to 0. If so, then at block 46, the computer may assign a binary 1 value to the corresponding member of the vector. However, if the computer determines that the key does not appear at least once (or at least the designated minimum number of times) in the molecule or that the labels for all components that participated in matching the key are set to 1, then, at block 48, the computer may assign a binary 0 value to the corresponding vector member.

In turn, at block 50, the computer may determine whether additional keys exist. If so, then, at block 52, the computer may advance to the next key and return to block 42. If not, then, at block 54, the computer may determine whether additional molecules exist. If so, then, at block 56, the computer may advance to the next molecule and return to block 36. If no additional molecules exist, then the computer may conclude that it has finished establishing descriptor vectors for at least the present iteration.

Of course, variations to this and other exemplary routines described herein are possible. For example, when establishing descriptions, the computer may deem to be absent from a molecule any substructure key that is wholly subsumed by another substructure key. As another example, the computer may create a feature vector for each molecule by first creating a real-number vector whose members indicate the number of times a respective key appears in the molecule, and then creating a bit-vector based on that real-number vector (where a member of the bit-vector is set to 1 if the corresponding member of the real-number vector is non-zero).

Further, as indicated above, the order of the routines described in this specification can be varied. As an example, the computer can establish descriptor vectors for each of the molecules in the input data set before selecting the actives (or other training set) to be pyramidally clustered. This change in order can be useful if the other non-selected molecules will later be used to test the pyramid or for other purposes where they may need to be described in any event.

d. Establishing Initial Clusters

To begin the pyramidal clustering process, the computer preferably first establishes in memory a plurality of clusters (nodes), each representing one of the molecules to be clustered. These clusters form a base of the pyramid. As the pyramidal clustering proceeds, the computer will generate additional clusters "on top" of these clusters until ultimately reaching a single cluster as the tip of the pyramid.

A cluster may take any of a variety of forms. As a general example, a cluster can simply be a data file, data record (e.g., in a database) or other data block in a memory or other data storage medium.

More specifically, each cluster object may take the form in memory of an object with attributes (e.g., fields of a database record). In the present example, these attributes can include, for instance, (i) a "cluster_ID" attribute, (ii) an "actives" attribute, (iii) a "cluster_vector" attribute, (iv) a "merged_status" attribute, (v) a "parent_ID" attribute, (vi) a "child1_ID"attribute, (vii) a child2_ID" attribute, (viii) a "learned_key" attribute, and (ix) an "activity" attribute. Some of these attributes may be null or undefined for various clusters.

The "cluster_ID" attribute can uniquely identify the cluster in the pyramid structure. In the exemplary embodiment, clusters are numbered with consecutive integers beginning with 0. The "actives" attribute is a list (e.g., an array) of the molecule(s) represented by the cluster, preferably by reference to the molecule IDs, which then correlate with a stored indication of the respective descriptor vectors and activity characteristics for the molecule(s).

The "cluster_vector" attribute is a description of the molecule(s) represented by the cluster. When the computer creates a cluster, the computer may be programmed to establish this description of the cluster, for use in comparing the cluster to other clusters, such as to measure the similarity between a pair of clusters. This description may also be referred to as an "object feature characteristic." For the singleton clusters, the cluser_vector may be equal to the descriptor vector established for the one molecule represented by the cluster. For non-singleton clusters, the cluster_vector may be some combination or function (e.g., average, sum of squares, etc.) of the descriptor vectors of the molecules represented by the cluster. As will be described more below, while this is one way to facilitate comparison of a non-singleton cluster to another cluster, other preferred methods exist as well.

The "merged_status" attribute indicates whether the node has been merged or not. In the exemplary embodiment, to start, the merged_status attribute of all singleton clusters is turned off (indicating that those clusters have not yet been merged). Once two clusters are merged together to form a new cluster, the merged_status attribute of each of the two clusters will be turned on, indicating that the clusters have been merged, and the merged_status attribute of the new cluster will be turned off, indicating that the new cluster has not yet been merged.

In an exemplary embodiment, each cluster (other than the final cluster at the tip of the pyramid) has a parent cluster into which it was merged, and each cluster (other than the starting, singleton clusters) is formed by the merger of two children clusters. Thus, the "parent_ID" attribute of a cluster is preferably the cluster_ID of its parent cluster, and the "child1_ID" and "child2_ID" of a cluster are preferably the cluster_IDs of its two children clusters. Alternatively, each cluster may have only a parent_ID or only child_IDs, as only one such indication is needed to indicate the relationship between parent and child clusters.

Finally, the "learned_key" attribute indicates the common substructure that the computer identifies based on an analysis of the molecules in the cluster, and the "activity_level" attribute indicates the activity level that the computer identifies as representative of the molecules in the cluster. The activity_level attribute may also be referred to as a "cluster activity characteristic."

e. Clustering

In the exemplary embodiment, the computer next performs multi-domain pyramidal clustering, beginning with the base level of singleton clusters. A variety of different clustering algorithms can be applied at this point, and, except to the extent claimed, the present invention does not necessarily require the use of any specific algorithm. By way of example, a suitable clustering algorithm is a multi-domain (fuzzy) version of the well known Wards agglomerative clustering algorithm. As described herein, the Wards clustering process is made multi-domain by allowing overlaps in clustering, as for instance when the computer detects a tie in proximity between cluster objects. This process may also be referred to as generalized pyramidal clustering ("GPC").

Figure 5:
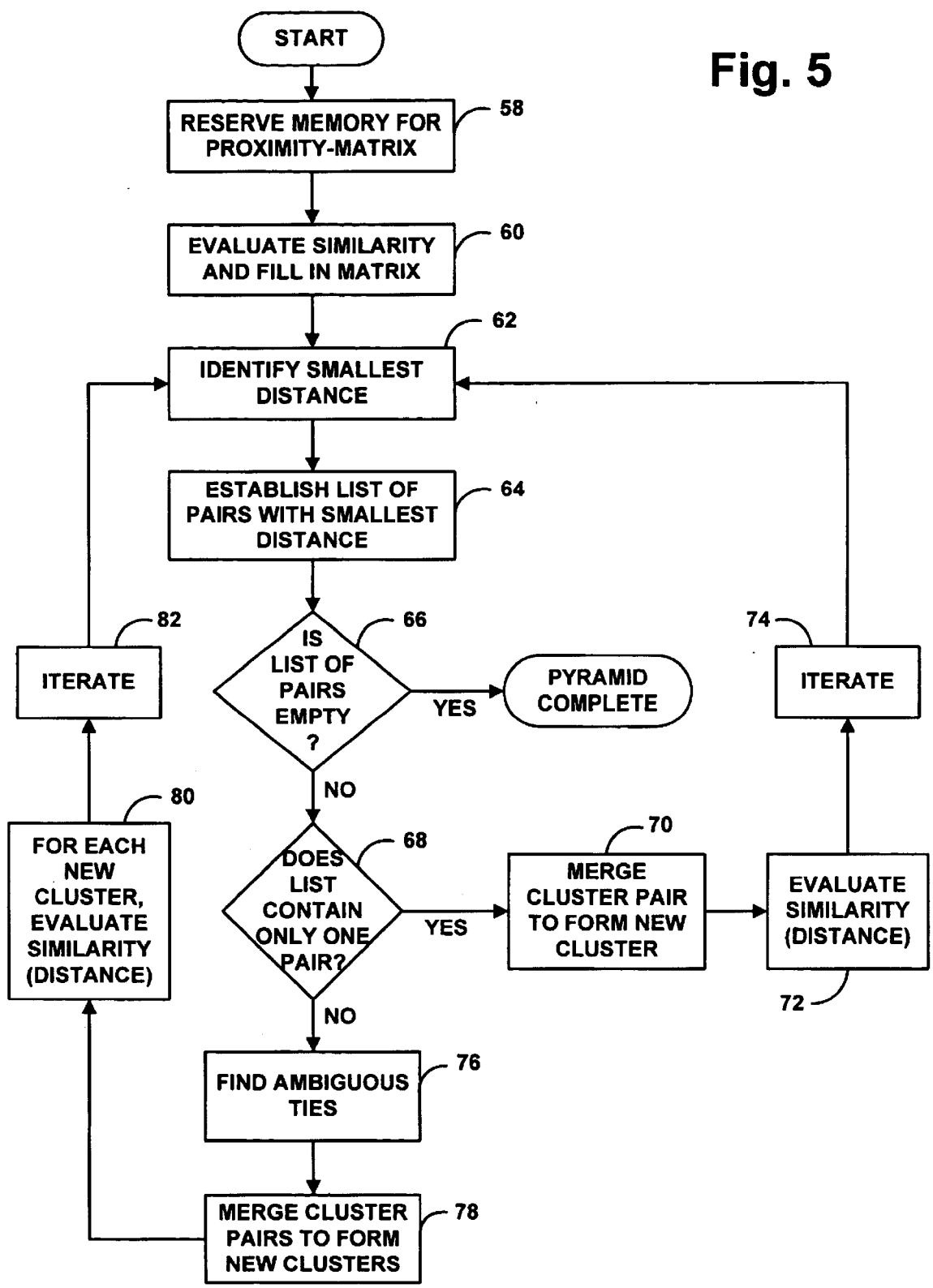
FIG. 5 is a flow chart illustrating an exemplary set of functions that a computer performs in the process of multi-domain clustering process according to an exemplary embodiment of the invention.

Referring to the drawings, FIG. 5 illustrates an exemplary set of functional blocks that may be involved in the multi-domain clustering process. As shown in FIG. 5, at block 58, the computer first reserves a space in memory for a proximity-matrix. The cells of the proximity matrix will indicate measures of similarity between clusters. Beginning with a base of 5 singleton clusters (as an overly-simplified example), the proximity-matrix can therefore be a 5×5 matrix, where the columns and rows each represent the 5 clusters.

At block 60, the computer then evaluates (measures, or computes) a dissimilarity between clusters in pairs and fills in (stores values in) the cells of the proximity-matrix accordingly. In the exemplary embodiment, the computer evaluates dissimilarity between a pair of clusters by measuring a distance between the clusters. As mentioned above, reference to "dissimilarity" or "similarity" in this context is really just a matter of perspective, since the ultimate goal is to determine which clusters are most alike. That determination can be made by finding which clusters are the least dissimilar or by finding which clusters are the most similar, and these methods should be viewed as being equivalent.

To compute the distance between two clusters, in the exemplary embodiment, the computer may compare the cluster_vector attributes of the clusters. The computer may employ any desired metric or algorithm to compute a distance (similarity/dissimilarity) between two clusters. By way of example, the computer can be programmed to compute a Euclidean distance between the two cluster_vectors. As another example, the computer can be programmed to compute a Tanimoto distance between the cluster_vectors. Other examples are possible as well, including but not limited to a Cosine coefficient and a Tversky coefficient for instance. Before beginning the pyramid-building process, the computer can prompt a user to select a desired comparison-metric and can then store an indication of the selected comparison-metric for later reference.

Alternatively, in a preferred embodiment, the comparison between two clusters can take the form of a more direct comparison between the molecules in the clusters (without the use of a "cluster_vector" type attribute). Thus, for instance, where both clusters in a given pair are singleton clusters, the evaluation of distance of the clusters can be simply a determination of how dissimilar the descriptor vectors of the respective molecules are from each other. Where at least one of the clusters of a given pair is a non-singleton cluster (containing two or more molecules), the evaluation of distance between the clusters can involve considering the distances between inter-cluster pairs of molecules.

For example, given cluster A that includes molecules 1 and 2, cluster B that includes molecules 3 and 4, and cluster C that includes molecule 5, to evaluate the distance among these clusters, the computer may consider molecular distances within the following inter-cluster pairs of molecules: 1-3, 1-4, 1-5, 2-3, 2-4, 2-5, 3-5 and 4-5. Depending on the desired d measure (e.g., Euclidean, Tanimoto, etc.), then, the computer may reach a conclusion about the distances between pairs of clusters.

Applying the complete-link technique, for instance, the computer may determine that, for cluster-pair A-B, distance 2-4 is the greatest, for cluster-pair A-C, distance 1-5 is the greatest, and for cluster-pair B-C, distance 4-5 is the greatest. The computer may therefore consider these greatest molecular pairwise distances to best define the distances between the respective clusters, and the computer may consequently record these representative distances in the proximity matrix. If, for example, the computer then determines that distance 2-4 (of cluster pair A-B) is smaller than both distance 1-5 (of cluster pair A-C) and distance 4-5 (of cluster pair B-C), then the computer may select cluster pair A-B as the pair with the smallest distance (greatest similarity). Other suitable comparison exist or will be developed in the future as well.

The evaluation of similarity/dissimilarity between a pair of molecules can involve comparing the descriptor vectors representing the molecules, which may involve computing distances such as Euclidean distances, Tanimoto distances, Tversky coefficients, Euclidean-Soergel products, and/or Euclidean-Tanimoto products, for instance. Alternatively, the evaluation may involve a comparison of physical molecular properties, such as 3D volumes, molecular force field shapes, and other spatial distributions of molecular properties.

The computer preferably limits its computation of distances to those clusters that have a non-merged status, i.e., those clusters whose merged_status is off. This is because, once a cluster has been merged with one or more other clusters, the information defined by the cluster has been used in the pyramid-building process. The computer may therefore disregard a merged cluster when continuing to build the pyramid. Thus, for instance, the computer might set a flag in each entry of the proximity-matrix that involves a merged cluster, or, after merging a cluster, the computer might delete from the matrix the column and row involving the merged cluster. (The cluster into which that cluster was merged would then be eligible for comparison with other clusters.)

For each pair as to which the computer measured a distance, the computer stores in the matrix a distance value. For instance, continuing with the above example of 5 base clusters, 0, 1, 2, 3 and 4, the computer may compute a distance between clusters 0 and 3 and may record the distance in the matrix at column 0, row 3. Alternatively, the computer may record its distance measurements in another form, such as in a data file or list.

At block 62, the computer then searches through the proximity-matrix to identify the smallest entry value (SEV) in the matrix, which represents the greatest similarity or smallest distance between two clusters. More than one entry in the matrix (i.e., more than one pair of the clusters) might have this smallest value.

At block 64, the computer then establishes in memory a list of the pairs of clusters for which the computer measured that greatest similarity.

In doing this, the computer could be arranged to select only those pairs that have exactly the same greatest similarity. Alternatively, however, the computer could be programmed to select those pairs that have substantially the same greatest similarity, possibly differing from the SEV by some statistical range. Before building the pyramid, the computer may prompt a user to specify this range and may store an indication of this range for later reference. The effect of extending the analysis in this way (i.e., broadening the scope of what constitutes the "smallest distance", "least dissimilarity" or "greatest similarity") is to render the resulting pyramid more fuzzy, i.e., to allow more multi-domain overlapping among clusters.

At block 66, the computer then determines whether the list of pairs established at block 64 is empty, which would indicate that no pairs of clusters remained to be evaluated. If the computer finds that the list of pairs is empty, then the computer may conclude that it has finished clustering the molecules and may proceed to the structure-learning process below. Otherwise, the computer proceeds to block 68.

At block 68, the computer determines whether the list of pairs contains only one pair. If so, then, at block 70, the computer merges the clusters of that one pair together to form a new cluster. Upon forming the new cluster, the computer then turns on (sets to one) the merged_status of the two merged clusters and turns off (sets to zero) the merged_status of the new cluster. At block 72, the computer then evaluates distances between the new cluster and each of the other clusters, as above, and records distance measures in the proximity-matrix (in a new row and column corresponding to the new cluster). At block 74, the computer then iteratively repeats the process, returning to block 62 to find the smallest entry value in the matrix.

If the computer determines at block 68 that the list contains more than one pair of clusters, then, at blocks 76 and 78, the computer proceeds to evaluate how to merge the clusters together and merges the clusters accordingly. To some extent, there may be no overlap between the pairs in the list. For instance, if the list contains two pairs, the pairs might be (i) clusters 1 and 2 and (ii) clusters 0 and 4. In that case, the computer preferably merges clusters 1 and 2 together to form one new cluster and separately merges clusters 0 and 4 together to form another new cluster. Upon performing each merging operation, the computer sets merged_status. attributes, and the computer evaluates similarities.

However, given a fairly homogeneous data set and bit-vector descriptions of the molecules, a great likelihood exists that there will be some overlap between the pairs in the list, reflecting a tie in proximity. (This tie may be an exact tie or a fuzzy tie, depending on the freedom with which the computer is instructed to identify pairs as having the "greatest similarity"). Thus, at block 76, the computer may seek to find any ties in proximity. For instance, the list might contain a pair of clusters 1 and 3 and a pair of clusters 2 and 3 (so that both pair includes cluster 3). In each such instance, the computer may still separately merge the pairs to form new clusters. To do so, the computer may clone (make another copy in memory of) the cluster that is involved with the tie, which, in the above example, would be cluster 3. The computer may then use one copy of the cluster in each of the merges for the tie. At block 78, the computer thus merges cluster pairs to form new clusters. And again, upon performing each merging operation, the computer sets the merged_status attributes, and the computer evaluates similarities.

At block 80, the computer then evaluates distances between each new cluster and each of the other clusters, as above, and records distance measures in the proximity-matrix (in a new row and column corresponding to the new cluster). At block 82, the computer then iteratively repeats the process, returning to block 62 to find the smallest entry value in the matrix.

As an added measure of efficiency, the computer may, at each level of the pyramid, determine whether the SEV is greater than a predefined threshold distance. If so, it may be reasonable to conclude that merging any clusters together would not prove sufficiently useful to justify continuing. Therefore, the computer may be arranged to stop the pyramid-building process at that point. The threshold distance can be hard coded or can be provided by a user in response to a prompt.

In an exemplary embodiment, the computer grows the proximity-matrix as it establishes new clusters.

Alternatively, to speed up the process, when the computer establishes the matrix in memory, the computer can reserve extra space for new rows and columns that the computer expects to add. One way to guess at the size, each time data is added to the matrix, is to subtract 1 from the number of non-merged clusters. Thus, for instance, if 5 clusters remain non-merged, the computer might add an additional 4 rows and columns to the matrix.

f. Learning Substructures

Once the computer has finished building the pyramid, the computer preferably identifies a chemical substructure common to the molecules in each cluster. Alternatively, the computer may identify a common substructure for each cluster once the computer establishes that cluster, or at another desired time. A set of parallel computer processors may be employed advantageously to carry out pyramid-building while concurrently analyzing clusters to identify common substructures. Alternatively, a single processor can be employed. A "processor" or "computer" should be understood to be one or more processors or computers.

The idea here is to discover a composite structure of components (e.g., atoms, bonds, spatial orientations, and/or other features (whether 2D or 3D in nature)) that best represents the structural similarities of the molecules in a cluster and that, therefore, most likely correlates with the observed activity of those molecules. In an exemplary embodiment, this composite structure is not just the similar components in the molecules of the given cluster (although it could be). Rather, because the exemplary embodiment is particularly interested in chemical reactions, the process of learning the composite structure may preferably take into consideration where in the molecules the components occurred.

For instance, several molecules in a cluster may have several components in common, but these components might not be part of the same substructure in all the molecules. In that case, the computer may reasonably conclude that there is no composite structure of interest in all of the molecules. However, if the computer determines that a significant set of components common to all the molecules in the cluster are involved in matching a larger composite substructure that appears in a relatively large number (preferably all) of molecules in the cluster, then the computer may reasonably conclude that the composite structure is of particular interest.

The result of clustering with descriptor vectors that are based on MACCS-like keys (e.g., SMARTS strings) is clusters of molecules with somewhat similar structures. However, the MACCS-like keys are unable to differentiate between structurally dissimilar molecules that set the same keys in the descriptor vector. This happens quite often because the keys are "redundant," describing small substructures of the molecule with multiple keys. A more representative feature of the molecules is the maximum common substructure (MCS) that is contained in all of the molecules in a cluster (i.e., the largest contiguous subgraph common to all the molecules (graphs)). Therefore, in accordance with an exemplary embodiment, a computer should seek to find the MCS among the molecules within each cluster. If the computer finds a most common composite structural component in a cluster, the computer may reasonably conclude that the structure is correlated with (or responsible for) the structural categorization of the molecules.

In an exemplary embodiment, the computer may identify an MCS among a set of molecules by identifying all substructures that the molecules have in common and then selecting the largest of those common substructures. The computer may thus employ an exhaustive common substructure search algorithm to find all substructures that the molecules of the cluster have in common. Of the common substructures thus identified, the computer then selects the largest common substructure. The determination of which substructure is the "largest" might depend on any desired factor(s), such as the number of atoms and bonds in each identified substructure for instance.

Other procedures can be used, of course, to identify a representative substructure for a given cluster. For instance, a genetic algorithm can be used to approximate a determination of an MCS, based on the structures of the molecules in the cluster.

It should be understood that reference to "substructure" throughout this specification could extend equally to 2-D (fragment-based) molecular structures as well as 3-D molecular feature sets, such as strengths of bonds, orientations, and so forth. In that case, the concept of "largest" substructure may be equivalently extended to other measures, such as "strongest bonds" or the like.

The substructure that the computer identifies for a given cluster can be either contiguous or non-contiguous. For instance, the substructure might be of the type R1-X-R2, where R1 and R2 are possibly contiguous substructures, and X is any structure coupling R1 to R2.

Upon identifying the MCS, the computer records an indication of the MCS as the learned_key attribute of the cluster. This recorded indication can take any of a variety of forms. By way of example, the learned_key attribute can be an ASCII string, such as a SMARTS string representation of the structure.

Although the exemplary embodiment involves identifying only a single MCS for each cluster, the invention may extend as well to identifying more than one common substructure for a cluster. For instance, where two substructures tie as the largest common substructure among the molecules in a cluster, it would be useful to store (and provide as output) indications of both common substructures.

g. Identifying-Representative Activity Levels

In addition to identifying a representative common substructure among the molecules in each cluster, the computer preferably identifies an activity level representative of the molecules in the cluster. The representative activity level can take a variety of forms. For instance, the activity level could be the average of the activity levels of the molecules in the cluster. Other algorithms could be applied as well.

As with the discovery of common substructures, the computer can establish a representative activity level per cluster after fully building the pyramid or as the computer builds the pyramid, such as through parallel processing. For each cluster, the computer then preferably stores the representative activity level in memory as the cluster's "activity" attribute.

h. Trimming the Pyramid

As noted above, once the computer has clustered the molecules into a pyramid structure (or at another desired time), the computer may trim from the pyramid those clusters that the computer deems to not provide useful information (or to not provide sufficiently useful information). An advantage of trimming the pyramid in this way is to eliminate extraneous data, and to thereby better assist a chemist or other person by providing more streamlined, focused output.

The judgement of what constitutes a cluster that does not provide sufficiently useful information and should therefore be trimmed can be based on various factors. As one example, the computer may deem to be of insufficient interest any cluster that has the same learned_key attribute as its parent, since both such clusters teach the same pharmacophore. In that scenario, the computer may eliminate the child cluster (for example) and change the child_pointers of the parent cluster to point to the children of the child cluster. On the other hand, a divergence in representative activity levels between such clusters might be of sufficient interest that the computer may be programmed to maintain both clusters.

As another example, the computer may deem to be of insufficient interest any singleton cluster, such as the initial clusters that form the base of the pyramid. Except in situations where the molecule represented by such a singleton cluster is vastly different from other molecules in the data set, a chemist is unlikely to be interested in such singleton clusters.

In an exemplary embodiment, any trimming of the pyramid can optionally be done only for purposes of output presentation (which is described more below). Thus, the entire untrimmed pyramid can be retained in a data storage medium for later reference or use, while an output display of the pyramid may show only a portion of the pyramid and omit trimmed portions.

i. Outputting Pharmacophoric Information

According to the exemplary embodiment, the computer may provide an output that is indicative of its findings. A multi-domain pyramid grown in the manner described above will advantageously define a number of structural families representing pharmacophoric subclasses. The information defined by the pyramid can be very useful to a chemist, as it can, for instance, assist in the discovery of beneficial new pharmaceuticals.

The computer preferably stores for output a variety of information concerning each cluster of the pyramid structure. This information can include, for example, (i) the list of actives in the cluster, (ii) the common substructure identified for the cluster, (iii) the representative activity level identified for the cluster, and (iv) pointers to the cluster's parent (if any) and children (if any).

The output may take any suitable form for conveying some or all of the useful information generated by the computer. By way of example, the output may take the form of a tree structure stored in a data storage medium (such as a computer memory, or optical or magnetic disk or tape), where each node in the tree can have parents and children. The root of the tree would be the tip of the pyramid, and children clusters would follow. In this regard, the output can be provided to a chemist in the form of a relational database file, where a table of the database may define as records the clusters of the pyramid structure. Each record may include fields indicative of attributes of the cluster such as those described above and may include a parent field and child field, indicating which records are the cluster's parent (if any) and child (if any).

As another example, a description of the pyramid can be provided as a file structure stored on diskette or other computer storage medium. Examples of such file structures are well known in the art and typically include readily accessible directories and subdirectories, each of which may include assorted files, properties and other information. Such file structures are particularly well suited to represent as a tree a pyramid of pharmacophoric-growth information generated in the manner described above. In particular, for instance, each directory can represent a single cluster of the pyramid, its subdirectories can represent its children cluster (if any), and its parent directory can represent its parent cluster (if any). One or more files or properties for the directory may include attribute information for the cluster as described above. For instance, each of the molecules (or its associated ID) may be contained within a respective file in the cluster's directory. Still further, each of the files or other portions of a directory can be arranged as a link (such as a shortcut or hyperlink) to other information such as images, graphs and descriptions of the molecules and keys associated with the cluster.

In an exemplary embodiment, a molecule viewer may also be provided, to allow a chemist or other person to view a 2D (or perhaps 3D) representation of a selected molecule in any given cluster. In addition, the whole pyramid structure can be displayed as a tree structure with an appropriate viewer.

A tree-viewer may be embodied as a software program executed by a computer processor, either integrally together with the pyramid-building system or as a separate module. In an exemplary embodiment, the tree-viewer would streamline the presentation of a tree structure to a chemist, by allowing the chemist to ask questions about the properties of individual tree nodes (clusters) and about the relationship between nodes, and by presenting the requested information visually on a computer monitor or other suitable display.

By way of example, a tree-viewer program could be written to present graphically on a computer monitor (or via a printer) a display of all or part of the tree structure. The program could provide various user options. For instance, the program could provide a FIND MOLECULE option that may prompt a user to enter a specific molecule ID or molecule description and may then responsively search the tree and visually present all nodes of the pyramid that contain (represent) the specified molecule. As another example, the program could provide EXPAND and CONTRACT options for each cluster, which may allow a user to selectively expand or contract a display of the tree so as to selectively see only a particular sub-tree. As yet another example, the program could allow a user to selectively view specified attributes of a given cluster or clusters. One such attribute may be the learned_key, presented as a chemical formula for instance. As still another example, the program could provide one or more TRIM options, which a user may select to direct the computer to trim from the output display various types of clusters (such as non-SAR rich children, singleton clusters, or the like).

In an exemplary embodiment, each cluster can be color coded (or otherwise emphasized) for display, with a color indicative of the difference between its average activity level (of the molecules it contains) and the average activity level of its parent cluster. Such color coding can thus conveniently define whether, based on the computer's analysis, the common substructure (pharmnacophore) of the cluster is activity-enhancing or activity-detracting in relation to the pharmacophore of its parent. Presentation of these conclusions in such a visually simple fashion is a great advantage, particularly when the input data set represents a vast amount of information that a chemist could quite likely not manually interpret.

A pyramid generated in the manner described above can beneficially embody structurally parsed indicia of each molecule in the input data set. Such information readily indicates through lineage in the pyramid the structurally important keys of each molecule, and how each key can progress to provide varying levels of activity. After the root cluster, and heading down the pyramid, each parent cluster in the tree that leads to a pair of children clusters may usefully provide an indication of how the common substructure (key) defining the parent cluster can be modified in practice to achieve a different pharmacophoric mechanism.

By tracing the lineage toward the root of the pyramid from any given cluster, one can readily determine a composite substructure that is likely to be responsible for classifying the family of molecules in the given cluster.

Phrased another way, in practice, the pyramid structure provides information to the end-user chemists in both its intermediate and terminal clusters. The intermediate levels (parent clusters) can be used to describe family resemblances among the molecules that are in lower clusters of that parent. This gives a more coarse level of description about what is similar among the molecules contained in that node or its descendents (i.e. lower nodes in the pyramid). The farther one progresses down into the tree, the more detailed and finer-grained the differences are that are drawn between groups of molecules.

A chemist may thus review the tree structure and conveniently see different ways to modify a molecule so as to perhaps achieve different levels of activity. Further, the computer can be programmed to depict for a chemist a core chemical structure as defined by a parent cluster in the pyramid, together with options of structural variations that may be likely to give rise to various levels of activity.

The computer may provide as output some or all of the information that it has gleaned in its analysis of the input data set. For instance, the computer can provide a description of the entire pyramid structure. Alternatively, for instance, the computer can provide a description of only one or more clusters or groups of clusters. In addition, the computer can provide its output entirely once it has finished building the pyramid and/or while it builds the pyramid. For example, each time the computer explores a new cluster, the computer can output its findings.

j. Testing the Pyramid

In accordance with an exemplary embodiment, the computer can be programmed further to test the resulting pyramid structure in order to evaluate the efficacy of the structure-to-activity relationships represented by the pyramid. One way to test the pyramid is to feed through the pyramid some or all of the inactive molecules from the input data set, i.e., those molecules that were not chosen for inclusion in the training set. Some or all of the inactive compounds may a flow through the pyramid (beginning with the root node) and land in one or more terminal clusters of the pyramid. This can be significant information for a chemist.

For example, if a given terminal cluster of the pyramid includes 1 highly active molecule, absent testing, it may be reasonable to conclude that the learned key that gave rise to that cluster correlates with the high activity level. However, if, for example, 30 inactive molecules fall into the same cluster, an expert may rightly conclude that the cluster was a false positive, i.e., the learned key of the node is not truly representative of high activity level. The computer may thus output an indication accordingly. The indication may, for instance, signal a need to use some other types of descriptors that could better correlate with activity. For example, if the computer employed a set of only 2-dimensional descriptors (e.g., not considering 3D orientation), a reasonable conclusion may be that the computer should employ a set of 3D descriptors. Alternatively, this result may lead to a decision to re-screen and/or to expand the library in that area so as to enable finer-level discrimination.

k. Using the Pyramid as a Multi-Domain Classifier

Once the computer has fully created the pyramid structure, it is finished learning. The pyramid structure may then usefully serve as a multi-domain classifier, to provide additional useful information to a chemist or other person.

At this stage, the computer may run a set of test molecule (s) through the pyramid to determine whether and where the test molecule(s) land within the pyramid. The test molecules could be molecules that have an unknown activity level, i.e., molecules that have not been subjected to the assay(s) to which the molecules of the training set were subjected. A given test molecule may fit neatly within one of the cluster of the multi-domain classifier (in that it includes all of the common substructures from the root cluster down to that cluster), which may support a conclusion that the molecule is likely to have an activity level similar to that indicated by the cluster (i.e., similar to the average activity level of the training molecule(s) that defined the "actives" attribute of the cluster).

On the other hand, a given test molecule may not fit within any cluster of the classifier. If that happens, the computer may deem such a molecule to be an outlier and may output an indication accordingly. The identification of outliers is a significant outcome, particularly if the test molecule turns out to be an active molecule.

Of course the computer may perform other testing and post-processing functions as well with respect a pyramid structure generated in accordance with the present invention.

3. Exemplary Pseudo-Code

Although the foregoing description of an exemplary embodiment will enable a person of ordinary skill in the art to readily make and use the invention, the following exemplary pseudo-code listing is provided for additional understanding. It should be understood that this pseudo-code depicts only one or more possible methods of carrying out an exemplary embodiment of the invention (and may differ in some respects from the description provided above). The pseudo-code is not intended to be limiting in any respect.

In this pseudo-code listing, the number of molecules in an exemplary data set is n, the number of original keys is m, and each key is weighted with a value of 1.

Exemplary Pseudo-Code Listing

Copyright© 2000 Bioreason, Inc.

1. Create a Feature Vector Describing Each Molecule

For every molecule in the data set, molecule$_y$, where y increments from 1 to n:

Initially create a feature vector of length m, so that there is one bit for each of the keys that will be used to describe the molecule. Initially set the value of each bit to be 0.

Establish a label A for each atom in molecules$_y$. Initially set the label A to be 0.

For every original substructure key, original_key$_z$, where z increments from 1 to m:

Search the Daylight SMILES representation of molecule$_y$ with the Daylight SMARTS representation of the original_key$_z$.

Identify the atoms in molecule$_y$ that participated in matching original_key$_z$.

If the original_key$_z$ is found at least once in molecule$_y$ and at least one atom that participated in matching the original_key$_z$ has a label A equal to 0, then set the bit z in the feature vector to be 1.

End for all substructure keys, original_key$_z$.

End for all molecules.

2. Clustering the Molecules Using a Multi-domain Generalized Pyramidal Clustering (GPC) Method Cluster the molecule$_y$ of the data set specified using the feature vectors prepared in step 1 and the GPC-wardsagglomerative-clustering method, to establish a fuzzy-agglomerative-cluster-tree (a GPC-pyramid). Follow the detailed steps below:

2.1. Assign each molecule in the specified data set to a cluster data object to form a unique, singleton cluster containing that molecule. Set each singleton cluster to non-merged status.

2.2. Compute the distance/proximity matrix p corresponding to the complete set of the singleton clusters by computing the distances of all possible pairs of singleton clusters. To compute the distance between two clusters use the feature vectors of the molecule contained in each cluster and the distance measure indicated by the user (e.g. Euclidean metric, Tanimoto coefficient, etc.)

2.3. Detect the closest pairs r1, r2, . . . rN of non-merged clusters by searching p and selecting all entries e1, e2, . . . eN in p that equal the smallest entry value (SEV) in p and where clusters c1 and c2 of each cluster pair r have a non-merged status.

2.4. Place the pairs of clusters r1, r2, . . . , rN in a list l 2.5.a. If there is no pair in list l then:
The clustering procedure is complete; the GPC-pyramid has been created; go to step 3

2.5.b. Else If there is only one pair r in list l then:
Create a new cluster c
Merge the pair r to form a new cluster and set that new cluster to c. Set cluster c to be non-merged
Set the status clusters c1 and c2 of pair r to merged
Use the wards agglomerative clustering method formula to compute the distance of new cluster c to all non-merged clusters. Store those distances in the proximity matrix p in a row/column corresponding to cluster c. If there is no row/column corresponding to c, then append to the proximity matrix a row/column corresponding to c.

2.5.c. Else if there is more than one pair in list l:
Detect all α-ties (ambiguous ties) among the pairs of clusters in list l, i.e. pairs in l of the type c1–c2 and c1–c3 indicating that cluster c1 is equidistant to both clusters c2 and c3.
Clone all α-clusters, i.e. clusters responsible for α-ties like c1, as many times as needed to produce one duplicate of the α-cluster for each pair in list l that it is a member of.
For each cluster pair r in list l:
Create a new cluster c
Merge the pair r to form a new cluster and set that new cluster to c. In the case where pair r contains an α-cluster use only one of the copies/clones of that cluster.
Set the status clusters cl and c2 of pair r to merged
Use the wards agglomerative clustering method-formula to compute the distance of new cluster c to all non-merged clusters. Store those distances in the proximity matrix p in a row/column corresponding to cluster c. If there is no row/column corresponding to c, then append to the proximity matrix a row/column corresponding to c.
End for each cluster pair r in list l:
End if 2.6. Iterate; go to step 2.3

3. Learning New Keys
For each cluster N of the GPC-pyramid:
Apply an exhaustive common substructure search algorithm to find the common substructures of all the molecules in the cluster N.
Designate the largest common substructure as a new substructure key, and set the learned_key attribute of the cluster N to the new substructure key; the learned_key of the cluster N will serve as the descriptive key of all molecules in the cluster.
End for each cluster N of the GPC-pyramid.

4. Evaluate and Restructure the GPC-pyramid
If the user selections indicate that he/she wishes to trim the GPC-pyramid, then:
For each arc (logical pointer) A between a parent cluster and a child cluster of the GPC-pyramid tree:
Compare the learned_key attributes of the two clusters, referred to as the parent cluster p, and the child cluster c
If the learned_keys of clusters p and c are the same, then remove cluster c from the GPC-pyramid and redirect the children clusters of c (if any) to show cluster p as their parent.
End for each arc A of the GPC-pyramid tree.
End if 4. Conclusion An exemplary embodiment of the present invention has been described herein. It will be understood, however, that changes and modifications may be made thereto without deviating from the true spirit and scope of the invention as defined by the claims. For instance, where appropriate, individual elements, steps, functions, arrangements and so forth described herein may be substituted with other equivalent elements now known or later developed and may be expanded or modified in ways now known or later developed. All examples described herein are illustrative and not necessarily limiting.

Further, the claims should not be read as limited to the described order of elements unless stated to that effect. In addition, use of the term "means" in any claim is intended to invoke 35 U.S.C. §112, paragraph 6, and any claim without the word "means" is not so intended.

We claim:

1. A computer-operable method for identifying chemical substructures by analysis of a data set representing a plurality of chemical structures, the method comprising, in combination:

executing a computer program to pyramidally cluster representations of the chemical structures, so as to produce in a data storage medium a hierarchy of clusters each representing one or more of the chemical structures;

with respect to each of at least a plurality of the clusters of the hierarchy, analyzing the one or more chemical structures in the cluster and determining a chemical substructure representative of the one or more chemical structures in the cluster; and outputting for consideration by a person a description of at least a portion of the hierarchy and an indication of at least one of the representative chemical substructures determined in the preceding step.

2. A method as claimed in claim 1, wherein executing a computer program to pyramidally cluster representations of the chemical structures comprises:

comparing clusters, and merging together pairs of clusters having a greatest similarity; and determining, at a given level of the hierarchy, that at least two pairs of clusters have substantially the same similarity, and responsively merging each pair respectively, to thereby form at least two new clusters at a next level of the hierarchy.

3. A method as claimed in claim 1, wherein executing a computer program to pyramidally cluster the representations comprises applying a clustering algorithm, the method further comprising, before applying the clustering algorithm, receiving user input defining at least one aspect of the clustering algorithm.

4. A method as claimed in claim 3, wherein the at least one aspect of the clustering algorithm comprises an identification of the clustering algorithm.

5. A method as claimed in claim 3, wherein the at least one aspect of the clustering algorithm comprises a fuzziness parameter.

6. A computer-operable method for identifying pharmacophoric mechanisms through analysis of a plurality of molecules, each molecule having a respective feature characteristic and a respective activity characteristic, the method comprising, in combination:
   (a) establishing in a computer memory a plurality of cluster objects, each cluster object representing one of the molecules;
   (b) agglomeratively clustering the cluster objects based on comparisons of the feature characteristics of the molecules that the cluster objects represent, to build in the computer memory a hierarchical pyramid comprising a plurality of cluster objects, each cluster object of the pyramid representing a number of the molecules;
   (c) with respect to each cluster object of a plurality of the cluster objects of the pyramid, identifying a substructure common to molecules represented the cluster object, each substructure defining a respective pharmacophoric mechanism; and
   (d) outputting for viewing by a person a description of at least a portion of the hierarchical pyramid, including at least one substructure identified in step (c).

7. A method as claimed in claim 6, wherein, the step of agglomeratively clustering the cluster objects comprises:
   to the extent any given cluster object is determined to be equidistant to a plurality of other cluster objects, merging the given cluster object with each cluster object of the plurality of other cluster objects.

8. A computer-operable method for identifying pharmacophoric mechanisms through analysis of a plurality of molecules, each molecule defining a feature characteristic and an activity characteristic, the method comprising the following steps:
   storing in a computer memory a plurality of data objects, each data object representing one of the molecules and having associated therewith a feature vector representing the feature characteristic of the molecule;
   pyramidally clustering the data objects based on their associated feature vectors, to form in the computer memory a pyramidal data structure comprising a number of nodes, each node representing one or more of the molecules;
   when pyramidally clustering the data objects, encountering a tie in proximity between a given node and at least two other nodes and responsively merging the given node separately with each of the at least two other nodes;
   with respect to each node of the pyramidal data structure, identifying a chemical feature set common to the one or more molecules represented by the node, the chemical feature set defining a pharmacophore; and
   providing an output describing at least a portion of the pyramidal data structure and including a description of the chemical feature set identified with respect to at least one node of the pyramidal data structure.

9. A computer-readable medium embodying a set of machine language instructions executable by a computer to identify pharmacophoric mechanisms through analysis of a plurality of molecules, each molecule defining a feature characteristic and an activity characteristic, wherein the machine language instructions are executable by the computer to perform functions comprising:
   storing in a computer memory a plurality of data objects, each data object representing one of the molecules and having associated therewith a feature vector representing the feature characteristic of the molecule;
   pyramidally clustering the data objects based on their associated feature vectors, to form in the computer memory a pyramidal data structure comprising a number of nodes, each node representing one or more of the molecules,
   when pyramidally clustering the data objects, encountering a tie in proximity between a given node and at least two other nodes and responsively merging the given node separately with each of the at least two other nodes;
   with respect to each node of the pyramidal data structure, identifying a chemical feature set common to the one or more molecules represented by the node, the chemical feature set defining a pharmacophore; and
   providing an output describing at least a portion of the pyramidal data structure and including a description of the chemical feature set identified with respect to at least one node of the pyramidal data structure.

10. A computer-operable method for learning pharmacophoric mechanisms through analysis of a plurality of molecules, each molecule having a respective feature characteristic and a respective activity characteristic, the method comprising, in combination:
   (a) selecting from the plurality of molecules a group of molecules having at least a threshold activity characteristic;
   (b) storing in a data storage medium a plurality of data objects each representing at least one of the molecules of the group, at least a first data object representing a plurality of molecules;
   (c) measuring distances between the data objects based on the feature characteristics of the molecules represented by the data objects, and making a determination that the distance between the first data object and a second data object is substantially equal to the distance between the first data object and a third data object;
   (d) in response to the determination, (i) storing in the data storage medium a fourth data object representing the molecules cooperatively represented by the first data object and the second data object and (ii) storing in the data storage medium a fifth data object representing the molecules cooperatively represented by the first data object and the third data object;
   (e) identifying at least (i) a common feature set among the feature characteristics of the molecules represented by the first data object and (ii) a common feature set among the feature characteristics of the molecules represented by the fourth data object, whereby each common feature set defines a respective pharmacophoric mechanism; and
   (f) providing to a person an indication of at least the common feature sets identified with respect to the molecules of the first and fourth data objects.

11. A method as claimed in claim 10, further comprising representing each feature characteristic as a binary vector having members indicating the presence or absence of respective molecular features.

12. A method as claimed in claim 11, wherein measuring distances between the data objects comprises computing a distance between a pair the data objects based on the binary vectors of the molecules represented by the data objects of the pair.

13. A method as claimed in claim 11, wherein measuring distances between data objects comprises computing a Tanimoto distance between a pair of the data objects.

14. A method as claimed in claim 11, wherein measuring distances between data objects comprises computing a Euclidean distance between a pair of the data objects.

15. A method as claimed in claim 11, wherein representing each feature characteristic as a binary vector comprises generating and storing the binary vector.

16. A method as claimed in claim 11, further comprising:
determining an object activity characteristic representative of the activity characteristics of the molecules represented by the first data object; and
determining an object activity characteristic representative of the activity characteristics of the molecules represented by the fourth data object.

17. A method as claimed in claim 16, further comprising determining a differential between the object activity characteristics determined with respect to the first and fourth data objects.

18. A method as claimed in claim 17, further comprising providing to the person an indication of the differential, whereby the person may correlate the differential with the common feature set identified with respect to the first data object.

19. A method as claimed in claim 10, wherein measuring distances between the data objects comprises measuring a distance between the first data object and the second data object, and, wherein, measuring a distance between the first data object and the second data object comprises applying a process selected from the group consisting of (i) Wards, (ii) complete-link, (iii) group average link, (iv) single link, and (v) centroid.

20. A method as claimed in claim 10, wherein storing in the data storage medium a plurality of data objects each representing at least one of the molecules of the group comprises developing a representation of each molecule and agglomeratively clustering the representations into the plurality of data objects.

21. A computer-operable method for analyzing a plurality of molecules, each molecule having a respective feature characteristic and a respective activity characteristic, wherein the respective activity characteristic of each molecule represents at least a threshold activity level, the method comprising, in combination:

(a) storing in a computer memory a plurality of cluster objects, each cluster object representing at least one of the molecules;

(b) conducting a merging process with respect to the cluster objects, the merging process comprising:
(i) comparing pairs of the cluster objects and, for each pair, measuring a respective dissimilarity between the cluster objects within the pair based on the feature characteristics of the molecules represented by the respective cluster objects;
(ii) of the dissimilarities measured in step (i), identifying a smallest dissimilarity;
(iii) selecting at least one pair of the cluster objects that has the smallest measured dissimilarity; and
(iv) with respect to each of the at least one pair selected in step (iii), merging the cluster objects of the pair to establish a cluster object cooperatively representing the molecules that were represented by the cluster objects of the pair;

(c) if at least two cluster objects have not yet been merged, then repeating step (b) with respect to the cluster objects that have not yet been merged;

(d) with respect to at least each cluster object established in step (b)(iv), identifying a common substructure among the molecules represented by the cluster object; and (e) outputting a description of at least one cluster object established in step (b)(iv), wherein, the description of each of the at least one cluster object comprises a first portion indicating the common substructure identified in step (d) for the cluster object.

22. A method as claimed in claim 21, further comprising:
establishing for each molecule a feature vector representing the feature characteristic of the molecule,
wherein measuring a respective dissimilarity between the cluster objects within the pair based on the feature characteristics of the molecules represented by the respective cluster objects comprises comparing the feature vectors of molecules represented by the cluster objects of the pair.

23. A method as claimed in claim 22, wherein each feature vector is a bit-string.

24. A method as claimed in claim 22, wherein measuring a respective dissimilarity between the cluster objects within the pair comprises computing a Euclidean distance between the cluster objects within the pair.

25. A method as claimed in claim 22, wherein measuring a respective dissimilarity between the cluster objects within the pair comprises computing a Tanimoto distance between the cluster objects within the pair.

26. A method as claimed in claim 22, wherein measuring a respective dissimilarity between the clusters objects within the pair comprises applying a comparison process selected from the group consisting of (i) Wards, (ii) complete-link, (iii) group average link, (iv) single link, and (v) centroid.

27. A method as claimed in claim 26, wherein identifying a common substructure among the molecules represented by the cluster object comprises identifying a chemical structure present in all of the molecules in the group.

28. A method as claimed in claim 27, wherein the chemical structure comprises an arrangement of atoms and bonds.

29. A method as claimed in claim 28, wherein the arrangement of atoms and bonds is a contiguous arrangement.

30. A method as claimed in claim 21, wherein outputting a description of at least one cluster object established in step (b)(iv) comprises providing output data representing at least all of the cluster objects established in step (b)(iv).

31. A method as claimed in claim 21, wherein outputting a description of at least one cluster object established in step (b)(iv) comprises presenting to a person a graphical depiction of cluster objects, the graphical depiction including for each cluster object an indication of the common substructure established with respect to the cluster object.

32. A method as claimed in claim 21, wherein outputting a description of at least one cluster object established in step (b)(iv) comprises presenting to a person a graphical depiction of cluster objects, the graphical depiction including for each cluster object an indication of a measure of the activity characteristics of the molecules represented by the cluster object.

33. A method as claimed in claim 21, wherein outputting a description of at least one cluster object established in step (b)(iv) comprises displaying a tree structure having nodes reflecting the cluster objects established in step (b)(iv).

34. A method as claimed in claim 21, wherein the description of each of the at least one cluster object further comprises a second portion indicating a measure of the activity characteristics of the molecules represented by the cluster object.

35. A method as claimed in claim 21, further comprising measuring an activity differential between a cluster object established in step (b)(iv) and a cluster object merged into the cluster object established in step (b)(iv).

36. A method as claimed in claim 35, wherein measuring the activity differential comprises comparing a measure of the activity characteristics of the molecules represented by the cluster object established in step (b)(iv) with a measure of the activity characteristics of the molecules represented by the cluster object merged into the cluster object in step (b)(iv).

37. A method as claimed in claim 35, wherein the description further comprises a second portion indicating the measure of activity differential between a cluster object established in step (b)(iv) and a cluster object merged into the cluster object established in step (b)(iv).

38. A computer-readable medium embodying a set of machine language instructions executable by a computer to analyze a plurality of molecules, each molecule having a respective feature characteristic and a respective activity characteristic, wherein the respective activity characteristic of each molecule represents at least a threshold activity level, wherein the machine language instructions are executable by the computer to perform functions comprising:

(a) storing in a computer memory a plurality of cluster objects, each cluster object representing at least one of the molecules, (b) conducting a merging process with respect to the cluster objects, the merging process comprising:

(i) comparing pairs of the cluster objects and for each pair, measuring a respective dissimilarity between the cluster objects within the pair based on the feature characteristics of the molecules represented by the respective cluster objects;

(ii) of the dissimilarities measured in step (i), identifying a smallest dissimilarity, (iii) selecting at least one pair of the cluster objects that has the smallest measured dissimilarity; and (iv) with respect to each of the at least one pair selected in step (iii), merging the cluster objects of the pair to establish a cluster object cooperatively representing the molecules that were represented by the cluster objects of the pair;

(c) if at least two cluster objects have not yet been merged, then repeating step (b) with respect to the cluster objects that have not yet been merged;

(d) with respect to at least each cluster object established in step (b)(iv), identifying a common substructure among the molecules represented by the cluster object; and (e) outputting a description of at least one cluster object established in step (b)(iv), wherein, the description of each of the at least one cluster object comprises a first portion indicating the common substructure identified in step (d) for the cluster object.

39. A processing system for screening a data set representing a plurality of molecules, in order to assist in identifying sets of molecular features that are likely to correlate with specified activity, the data set defining, for each represented molecule, a feature characteristic and an activity characteristic, the processing system comprising, in combination:

at least one processor;

at least one data storage medium;

machine-language instructions stored in the at least one data storage medium and executable by the at least one processor to perform the following functions:

(a) storing in a computer memory a plurality of cluster objects, each cluster object representing one of the molecules;

(b) with respect to the cluster objects, conducting a merging process comprising:

(i) comparing pairs of the cluster objects and, for each pair, measuring a respective dissimilarity between the cluster objects within the pair, based on the feature characteristics of the molecules represented by the cluster objects of the pair;

(ii) of the dissimilarities measured in step (i), identifying a smallest dissimilarity;

(iii) selecting at least one pair of the cluster objects that has the smallest respective measured dissimilarity;

(iv) with respect to each pair of the at least one pair selected in step (iii), merging the cluster objects of the pair to establish a cluster object cooperatively representing the molecules that were represented by the cluster objects of the pair;

(c) if at least two cluster objects have not yet been merged, then repeating step (b) with respect to the cluster objects that have not yet been merged;

(d) with respect to at least each cluster object established in step (b)(iv) identifying a common substructure among the molecules represented by the cluster object; and (e) outputting a description of at least one cluster object established in step (b)(iv), wherein, the description of each of the at least one cluster object comprises a first portion indicating the common substructure identified in step (d) for the cluster object.

40. A processing system as claimed in claim 39, wherein the computer memory is the data storage medium.

41. A processing system as claimed in claim 39, wherein the description of each of the at least one cluster object further comprises a second portion indicating a measure of the activity characteristics of the molecules represented by the cluster object.

* * * * *